(12) United States Patent  
Blake et al.

(10) Patent No.: US 8,216,308 B2
(45) Date of Patent: *Jul. 10, 2012

(54) ACCOMMODATING ARTIFICIAL OCULAR LENS (AAOL) DEVICE

(75) Inventors: Larry W. Blake, Coto De Caza, CA (US); William C. Huddleston, Anaheim Hills, CA (US); Gene Currie, Anaheim Hills, CA (US)

(73) Assignee: Tekia, Inc., Irvine, CA (US)

( * ) Notice: Subject to any disclaimer, the term of this patent is extended or adjusted under 35 U.S.C. 154(b) by 1376 days.

This patent is subject to a terminal disclaimer.

(21) Appl. No.: 11/312,553

(22) Filed: Dec. 21, 2005

(65) Prior Publication Data

US 2006/0100704 A1    May 11, 2006

Related U.S. Application Data

(63) Continuation-in-part of application No. 10/942,992, filed on Sep. 17, 2004, now Pat. No. 7,435,258, and a continuation-in-part of application No. 11/249,358, filed on Oct. 14, 2005, now abandoned.

(51) Int. Cl.
*A61F 2/16* (2006.01)
(52) U.S. Cl. ....... 623/6.37; 623/6.4; 623/6.44; 623/6.46
(58) Field of Classification Search ........ 623/6.37–6.46, 623/6.4, 6.34
See application file for complete search history.

(56) References Cited

U.S. PATENT DOCUMENTS

| | | | |
|---|---|---|---|
| 6,660,035 B1 * | 12/2003 | Lang et al. | 623/6.37 |
| 6,849,091 B1 * | 2/2005 | Cumming | 623/6.21 |
| 7,150,760 B2 * | 12/2006 | Zhang | 623/6.37 |
| 2003/0135272 A1 * | 7/2003 | Brady et al. | 623/6.37 |

* cited by examiner

*Primary Examiner* — David H Willse
*Assistant Examiner* — Javier Blanco
(74) *Attorney, Agent, or Firm* — Klima Law Offices, P.L.L.C.

(57) ABSTRACT

An accommodating artificial ocular lens (AAOL) device including a moving lens optic portion connected to a lens plate haptic portion. Preferably, the lens optic portion is connected to the lens plate haptic portion by a pair of flexible or resilient transverse oriented lens arm portions to provide or allow for movement of the lens optic portion.

22 Claims, 12 Drawing Sheets

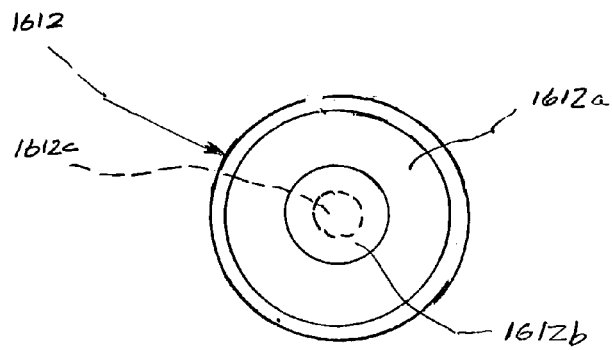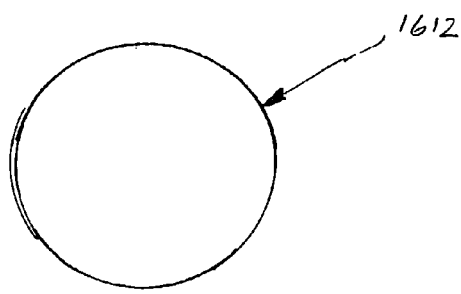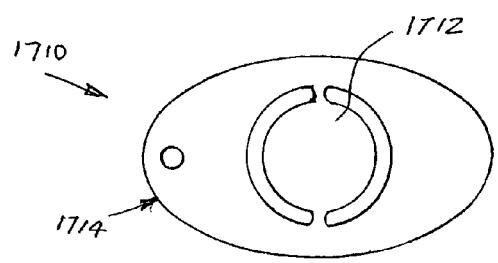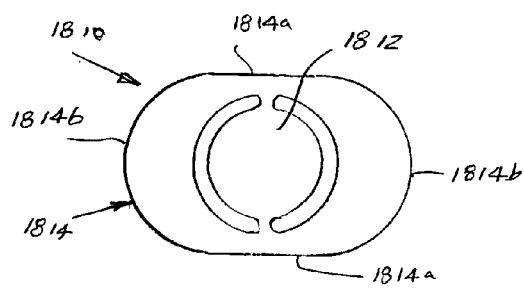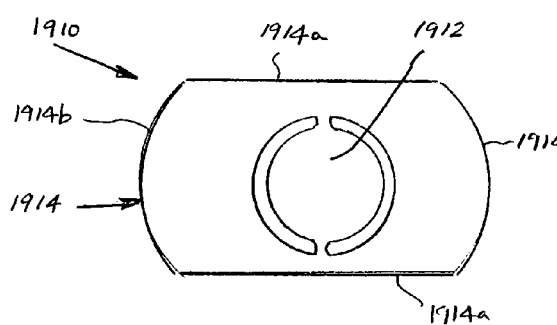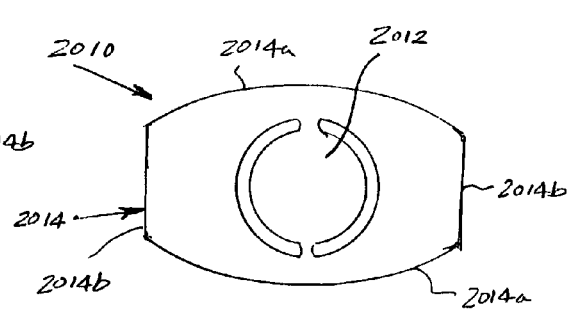

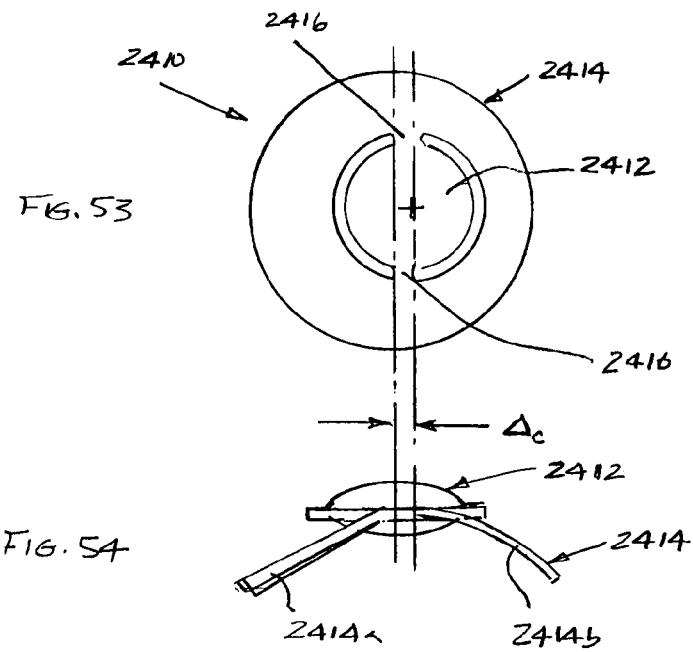
FIG. 53
FIG. 54
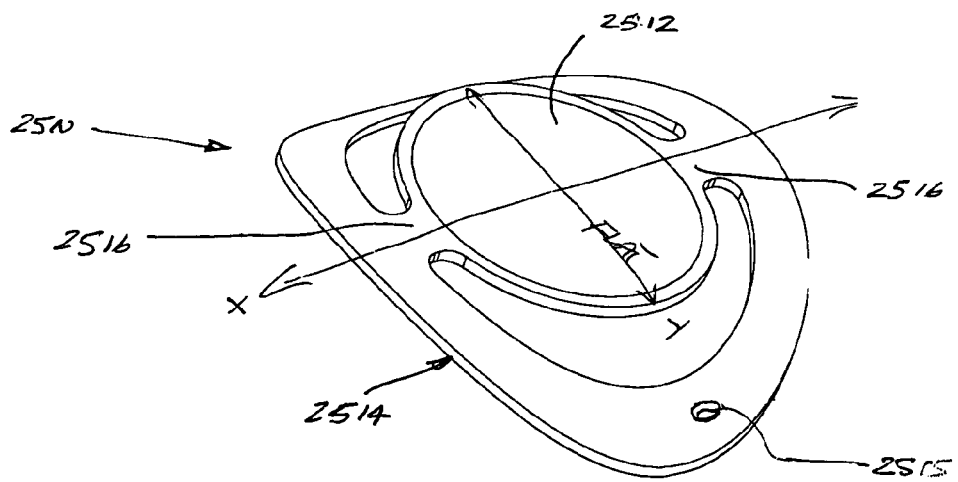
FIG. 55
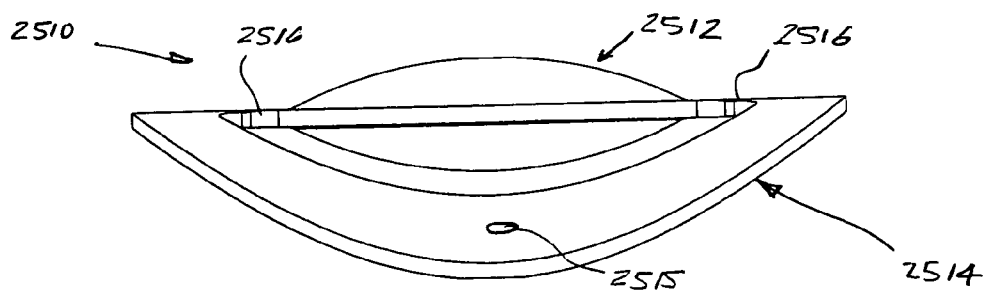
FIG. 56

ACCOMMODATING ARTIFICIAL OCULAR LENS (AAOL) DEVICE

RELATED APPLICATION(S)

This is a continuation-in-part of U.S. patent application Ser. No. 10/942,992 entitled "An Accommodating Intraocular Lens Device" filed on Sep. 17, 2004, now U.S. Pat. No. 7,435,258, and U.S. patent application Ser. No. 11/249,358 entitled "Refractive Corrective Lens (RCL)" filed on Oct. 14, 2005 now abandoned, and both applications are fully incorporated by reference herein.

FIELD OF THE INVENTION

The present invention is directed to an artificial ocular lens (AOL), in particular an accommodating artificial ocular lens (AAOL) device. A preferred embodiment of the accommodating artificial ocular lens (AAOL) device according to the present invention includes a posterior chamber accommodating artificial ocular lens (pc-AAOL) device for use in the posterior chamber of the eye outside the capsular bag or inside the capsular bag (i.e. after cataract or clear natural lens removal). Preferably, the accommodating artificial ocular lens (AAOL) according to the present invention is a deformable accommodating artificial ocular lens (AAOL) for implantation through a small incision in the eye.

BACKGROUND OF THE INVENTION

Currently, there exists a high level of cataract lens surgeries performed in the United States and in other countries and territories throughout the world. These cataract lens surgeries involve the removal of the natural crystalline lens, typically by phacoemulsification, followed by the implantation of an intraocular lens (IOL).

Most cataract lens surgeries are performed using an intraocular lens providing little if any accommodation of the eye. Specifically, the intraocular lens is implanted into the capsular bag of the eye, and once healing of the eye has occurred, there is very little movement of the intraocular lens in a manner to focus the eye by accommodation like the natural crystalline lens of the eye.

There has been much interest in creating and designing intraocular lenses (IOLs) configured to provide accommodation the same or similar to the natural crystalline lens of the eye. It is believed that the next generation of intraocular lenses (IOLs) will be accommodating intraocular lenses (AIOLs) that will provide a significant amount of accommodation of at least one (1) diopter or more. So far, most accommodating intraocular lenses (AIOLs) being clinically studied provide one (1) diopter or less of accommodation of the eye. Thus, there now exists a need for an accommodating intraocular lens that can provide a substantial amount of accommodation of the eye, desirably, providing one (1) or more diopters of accommodation of the eye. Further, there now exists a need for an accommodating artificial ocular lens (AAOL) configured to be inserted into the posterior chamber of the eye outside the capsular bag with the natural lens in place or removed, or inside the capsular bag.

The present invention is directed to an accommodating artificial ocular lens (AAOL) device such as an accommodating intraocular lens (AIOL) device configured in a manner that may provide for substantial accommodation of the eye.

SUMMARY OF THE INVENTION

A first ($1^{st}$) object of the present invention is to provide an improved accommodating artificial ocular lens (AAOL).

A second ($2^{nd}$) object of the present invention is to provide an accommodating artificial ocular lens (AAOL) including an lens optic portion flexibly or resiliently connected to a lens plate haptic portion.

A third ($3^{rd}$) object of the present invention is to provide an accommodating artificial ocular lens (AAOL) including an lens optic portion flexibly or resiliently connected to a lens plate haptic portion configured to bow within the eye to provide accommodation of the eye.

A fourth ($4^{th}$) object of the present invention is to provide an accommodating artificial ocular lens (AAOL) including a lens optic portion connected to a bowing lens plate haptic portion configured to bow within the eye and move said lens optic portion to provide accommodation of the eye.

A fifth ($5^{th}$) object of the present invention is to provide an accommodating artifical ocular lens (AAOL) including a lens optic portion connected to a lens plate haptic portion configured to bow relative to a length axis of the accommodating artificial ocular lens (AAOL).

A sixth ($6^{th}$) object of the present invention is to provide an accommodating artificial ocular lens (AAOL) including a lens optic portion connected to a lens plate haptic portion configured to bow relative to a width axis of the lens plate haptic portion.

A seventh ($7^{th}$) object of the present invention is to provide an accommodating artificial ocular lens (AAOL) including a lens optic portion connected to a lens plate haptic portion configured to bow relative to both the length axis and width axis of the lens plate haptic portion.

An eighth ($8^{th}$) object of the present invention is to provide an accommodating artificial ocular lens (AAOL) including a lens optic portion connected to a lens plate haptic portion configured to bow in three-dimensions (3D) within the eye.

A ninth ($9^{th}$) object of the present invention is to provide an accommodating artificial ocular lens (AAOL) including a lens optic portion connected to a lens plate haptic portion, the lens plate haptic portion being a bowing lens plate haptic portion for moving said lens optic portion within the eye to provide accommodation of the eye.

A tenth ($10^{th}$) object of the present invention is to provide an accommodating artificial ocular lens (AAO) including a lens optic portion connected to a lens plate haptic portion by at least by one flexible arm.

An eleventh ($11^{th}$) object of the present invention is to provide an accommodating artificial ocular lens (AAOL) including a lens optic portion connected to a lens plate haptic portion and configured to move the lens optic portion relative to the lens plate haptic portion when force is applied to the edge of the lens plate haptic portion.

A twelvth ($12^{th}$) object of the present invention is to provide an accommodating artificial ocular lens (AAOL) including a lens optic portion connected to a lens plate haptic portion, the lens optic portion being separate and spaced apart from the lens plate haptic portion by a predetermined distance, the lens optic portion and the lens haptic portion being connected together by at least one flexible or resilient arm.

A thirteenth ($13^{th}$) object of the present invention is to provide an accommodating artificial ocular lens (AAOL) including a lens optic portion connected to a lens plate haptic portion, the lens optic portion being connected to said lens plate portion in a manner so that said lens optic portion tilts relative to a central optical axis of the eye when moved by said lens plate haptic portion during accommodation of the eye.

A fourteenth ($14^{th}$) object of the present invention is to provide an accommodating artificial ocular lens (AAOL) including a multi-focal lens optic.

A fifteenth (15$^{th}$) object of the present invention is to provide an accommodating artificial ocular lens (AAOL) including a multi-focal lens optic portion connected to a lens haptic portion.

A sixteenth (16$^{th}$) object of the present invention is to provide an accommodating artificial ocular lens (AAOL) including a multi-focal lens optic portion connected to a lens plate haptic portion.

A seventeenth (17th) object of the present invention is to provide an accommodating artificial ocular lens (AAOL) including a multi-focal lens optic portion connected to a lens haptic portion.

A eighteenth (18$^{th}$) object of the present invention is to provide an accommodating artificial ocular lens (AAOL) including a multi-focal lens optic portion connected to a lens plate haptic portion.

A nineteenth (19$^{th}$) object of the present invention is to provide an accommodating artificial ocular lens (AAOL) including a multi-focal lens optic portion connected to a lens plate haptic portion by at least one flexible or resilient lens arm portion.

A twentieth (20$^{th}$) object of the present invention is to provide an artificial ocular lens (AOL) made of an optically clear polyimide material.

The present invention is directed to an artificial ocular lens (AOL) device, in particular an accommodating artificial ocular lens (AAOL) device. For example, the present invention is directed to an accommodating artificial ocular lens (AAOL) device for implanting into the posterior chamber of the eye outside the capsular bag (with or without the natural lens removed) and an accommodating artificial ocular lens (AAOL) device for implanting into the capsular bag of the eye, or otherwise an accommodating intraocular lens (AIOL) device.

The accommodating artificial ocular lens (AAOL) device according to the present invention includes a moving lens optic portion. Specifically, the lens optic portion is supported for movement by a lens haptic portion. The lens optic portion is moved when the lens haptic portion is bowed or vaulted through used of flexible connecting arms connecting the lens optic portion to the lens haptic portion. The flexible connection arms move the lens optic portion forward and backward along the central focal axis of the eye during the accommodation process. In preferred embodiment, the lens optic portion is provide with at least one toric, multi-focal and/or wavefront features (e.g. modified or customized lens surfaces and/or lens interiors). Thus, the present invention provides for a moving toric, multi-focal and/or wavefront lens optics (e.g. translational and/or tilting and/or rotating movement of lens optic) providing a combined or even synergistic effect for increasing the extent, amount or degree of accommodation (e.g. less distance of movement required of lens optic to provide same degree of accommodation).

The accommodating artificial ocular lens (AAOL) device according to the present invention includes a lens optic portion connected to a lens haptic portion, preferably a lens plate haptic portion. The lens optic portion can be a hard intraocular lens optic made of a hard or non-deformable material (e.g. polymethylmethacrylate (PMMA) or hard type optically clear polyimide), or can be a soft or flexible or deformable intraocular lens optic made of a soft, flexible, resilient, foldable, compressible and/or otherwise a deformable material l, in particular a substantially deformable material (e.g. silicon, collagen-containing polymer, acrylic, polyimide, soft type polyimide, polyether, polyamide, polyester, polysulfone, polyethersulfone and other biological compatible materials of suitable refractive index).

A particularly preferred material for making the artificial ocular lens (AOL) device and accommodating artificial ocular lens (AAOL) device according to the present invention is an optically clear polyimide material having a refractive index of 1.5, more preferably 1.6, and most preferably 1.7 or higher. The polyimide material preferably has an optical transmittance of ninety percent (90%) or higher, a specific gravity of 1.2 (1.4 maximum), a durometer hardness of 40 to 60 shore A, a tensile strength of approximately 750 psi, an elongation of fifty percent (50%), a tear strength of 100 PPI (50 PPI minimum), and a water absorbtion of one percent (1%) maximum with hydrolytic stability. Further, the polyimide material should be foldable (i.e. folded onto itself for 5 minutes and then released), and sterilizable (i.e. not affected by standard 18 hr $8/12$ ethylene oxide cycles, or 1 hr standard 250 F autoclave cycles, and medical grade (i.e. not toxic, carcinogenic, or mutagenic).

The lens plate haptic portion is preferably made of a soft, flexible, resilient, foldable, compressible and/or deformable material, and configured to allow the lens plate haptic portion to bow when an inwardly directed force is applied to the edges or edge portions of the lens plate hapic portion and/or pressure is exerted on the back surface of the capsular bag to move the lens optic portion forward to provide accommodation of the eye. The accommodating artificial ocular lens (AAOL) device according to the present invention can be made as a single piece lens (e.g. by molding or machining), or can be made as a multiple-piece lens assembled together (e.g. hard or soft lens optic portion connected to a separate soft or deformable lens plate haptic portion made of a soft, flexible, resilient, foldable, compressible and/or deformable material).

In one embodiment, the lens optic portion of the accommodating artificial ocular lens (AAOL) device according to the present invention remains substantially fixed in size and shape (i.e. fixed conformation) after implantation into the eye, and also remains fixed during accommodation. Specifically, the lens optic portion remains in a fixed conformation, and is not itself bent or bowed once implanted in the eye while the lens haptic portion bows to move the lens optic portion. In this fixed lens optic portion conformation or arrangement, the lens optic portion provides stable or fixed optical characteristics or performance while moving or accommodating within the eye. However, it is to be noted that the lens optic portion, in particular for a soft or deformable type accommodating artificial ocular lens (AAOL) according to the present invention, can be substantially deformed, rolled, compressed or folded for insertion through a small incision (i.e. 3.5 mm or less) and then implanted into the eye.

In another embodiment, the lens optic portion can be configured to tilt (e.g. relative to capsular bag and/or lens plate haptic portion) to provide and/or improve accommodation or during accommodation within the eye. Specific, the lens optic portion is configured so that the optical power of the lens optic portion changes with increased angle of tilt from a reference plane set perpendicular relative to the optical axis of the eye. The lens optic portion can be configured so that the power of the lens optic portion is proportional to the angle of tilt, or alternatively, the lens optic portion can be configured so that the power of the lens optic portion changes exponentially to the angel of tilt.

The accommodating artificial ocular lens (AAOL) device according to the present invention includes a lens optic portion and a lens haptic portion, preferably a lens plate haptic portion. The lens optic portion is essentially a separate component from the lens haptic portion except for at least one flexible or resilient arm connecting the lens optic portion to the lens haptic portion. Preferably, at least one opening is provided between an outer edge of the lens optic portion and an inner edge of the lens plate haptic portion. More specifically, the lens optic portion is separated from the lens plate haptic portion by a predetermined fixed or varying distance or spacing. In this arrangement, the outer edge of the lens optic portion is able to move substantially freely and independently relative to the inner edge of the lens plate haptic portion except at the point or points of connection with the flexible or resilient arm(s). Preferably the sizing of the haptic is customized to the particular patient's eye.

The accommodating intraocular lens (AIOL) according to the present invention includes at least one arm, preferably a flexible or resilient arm connecting the lens optic portion to the lens plate haptic portion. The flexible or resilient arm is configured to move the lens optic portion along the central focus axis of the eye when the lens plate haptic portion is bowed, for example, when the eye exerts an inwardly directed radial force at one or more positions around the outer edge of the lens plate haptic portion. More specifically, the lens optic portion is moved back-and-forth along the central focal axis of the eye for purposes of accommodation for focusing the eye when the lens plate haptic portion is bowed and unbowed. At least one flexible arm allows the outer edge of the lens optic portion to move relative to the inner edge of the lens plate haptic portion, which becomes distorted as the lens plate haptic portion is bowed. In this manner, the at least one flexible or resilient arm undergoes tensile stress, shear stress, pressure, and some tortional stress when the lens plate haptic portion is bowed without breaking or without permanently deforming. Specifically, the stresses are at a level within the at least one flexible or resilient arm when the lens plate haptic portion is bowed so as to not cause plastic deformation of the at least one flexible or resilient arm. Thus, when the force on the outer edge of the lens plate haptic portion is relieved and/or pressure is relieved behind the lens, the stresses within the at least one arm are relieved and causes the lens optic portion to move back to a resting position relative to the eye.

In preferred embodiments of the accommodating artificial ocular lens (AAOL) device, the lens optic portion is initially located in the same plane as the lens plate haptic portion. When force is applied to the outer edge of the lens plate haptic portion, the lens plate haptic portion begins to bow and moves the lens optic portion out of the initial reference plane along the central focal axis of the eye. As the lens plate haptic portion bows, it changes shape substantially from a two-dimensional (2-D) configuration to a cupped or bowed three-dimensional (3-D) configuration, and is substantially no longer planar.

The outer periphery or edge portion of the lens plate haptic portion is preferably configured and/or treated to facilitate or enhance anchoring thereof within the eye. Specifically, the lens plate haptic portion can be provided with one or more through holes to allow tissue on either side of the lens plate haptic portion to adhere together in and through the hole. Alternatively, or in addition, the outer edge of the lens plate haptic portion can be provided with scallops, serrations, notches, protrusions, pins, fingers to facilitate tissue adherence thereto.

Further, preferably the outer edges of the lens plate haptic portion is provided with one or more shape edge portions. For example, the lens plate haptic portion is cut by stamping through the thickness of the lens plate haptic portion to form an upper sharp edge and lower sharp edge. The radius of curvature (i.e. bevel or blend) of these sharp edges is preferably twenty-five (25) microns or less, more preferably ten (10) microns or less, and most preferably five (5) microns or less. The sharper the upper and lower outer perimeter edges of the lens plate haptic, the better the lens plate haptic portion prevents the growth of cells onto the lens plate haptic and lens optic portion when the accommodating artificial ocular lens (AAOL) device is implanted in particular into the capsular bag.

The stamp for making the sharp edges of the lens plate haptic portion is preferably diamond polished at the cutting edges to desirably achieve a radius of curvature of twenty-five microns or less.

In preferred embodiments of the accommodating artificial ocular lens (AAOL) device according to the present invention, the lens haptic portion is circular-shaped or substantially rectangular shaped. Further, preferably the lens optic portion is centered relative to the shape of the outer periphery of the lens plate haptic portion.

Another preferred embodiment of the accommodating artificial ocular lens (AAOL) device according to the present invention includes a lens optic portion located off center in one or both the length and width dimensions of the lens plate haptic (i.e. relative to the outer perimeter shape of the lens plate haptic portion). In this manner the accommodating artificial ocular lens (AAOL) device can be customized to take into account the morphology of the interior of the eye of a particular patient in custom designing and prescribing the particular accommodating artificial ocular lens (AAOL) device for said patient.

A further preferred embodiment of the accommodating artificial ocular lens (AAOL) device according to the present invention includes a pair of flexible or resilient arms connecting the lens optic portion to the lens plate haptic portion, the lengths of the arm portions being the same or different to center or off-center the lens optic portion relative to the central optical axis of the eye. Further, the location of the pair of arm portions can be located along a center axis of the lens optic portion, or can be located off axis again to center or off-center the lens optic portion relative to the central optical axis of the eye.

An even further preferred embodiment of the accommodating artificial ocular lens (AAOL) device according to the present invention includes a lens optic portion connected to a lens plate haptic portion so that the lens optic portion is tilted relative to said lens plate haptic portion or central focal axis to provide accommodation by tilting and untilting of the lens optic portion changing its effective lens power. Specifically, the artificial ocular lens (AAOL) device is configured or designed to purposely tilt the lens optic to continuously increase the lens power linearly or exponentially proportional relative to the increase in tilting angle. For example, in some embodiments, the angle of tilt remains linear or fixed during bowing of the lens haptic portion, and in other embodiments, the angle of tilt progresses or regresses exponentially based on the extent of bowing of the lens haptic portion. In a further embodiment, the lens optic portion is not tilted relative to the central focal axis of the eye initially (e.g. lens optic portion is located in same plane as lens plate haptic portion initially), and then the lens optic portion progressively tilts relative to the central focal axis of the eye as the lens haptic portion is bowed.

A preferred embodiment of the accommodating artificial ocular lens (AAOL) device according to the present invention includes a multi-focal lens optic portion. The multi-focal lens optic portion provides two or more lens power once implanted in the eye (e.g. bifocal, trifocal, four or more lens powers or different power regions or zones).

The accommodating artificial ocular lens (AAOL) device according to the present invention can be configured to replace the natural crystalline lens of the eye (e.g. an accommodating intraocular lens (AIOL) device for implantation into the capsular bag or an accommodating artificial ocular lens (AAOL) device for implantation into the anterior or posterior chamber of the eye outside the capsular bag). Alternatively, the accommodating artificial ocular lens (AAOL) device according to the present invention can be an accommodating refractive correction lens (ARCL) device configured to be implanted into the eye with the natural crystalline lens intact or combined with an implanted intraocular lens (IOL) device as an additional or supplemental lens (i.e. multiple lens system, two lens system, three lens system, four or more lens system).

A preferred embodiment of the accommodating refractive correction lens (ARCL) device according to the present invention is a soft or deformable phakic accommodating refractive correction lens (pARCL) device (i.e. accommodating refractive correction lens device added to eye having a substantially healthy or fully functioning natural crystalline lens), or an aphakic supplemental accommodating refractive correction lens (ap-sARCL) device (i.e. accommodating refractive correction lens device added to an eye having an implanted IOL) configured to be implanted through a very small incision in the eye (i.e. 2 mm or less, or preferably 1 mm).

Another embodiment is a soft or deformable anterior chamber phakic accommodating refractive correction lens (ac-pARCL) device or aphakic supplemental accommodating refractive correction lens (ap-sARCL) device configured to be implanted through a very small incision in the eye.

A preferred embodiment of the accommodating artificial ocular lens (AAOL) device according to the present invention is a soft or deformable custom accommodating artificial ocular lens (c-AAOL) device configured to be implanted through a very small incision in the eye.

Specifically, a custom accommodating artificial ocular lens (c-AAOL) device according to the present invention preferably corrects at least two (2), and more preferably at least three (3) visual problems or defects (e.g. accommodating problems, optical problems, power problems, astigmatic problems, refractive problems, tissue problems, impairments, abnormalities, disease or other factors or conditions impairing or negatively affecting a patient's vision). In a preferred embodiment of the custom accommodating artificial ocular lens (c-AAOL) device according to the present invention, a patient's vision may be corrected to 20:20, more preferably to 20:10, and even possibly to 20:7 and/or best correctable vision and the patient regains substantial to complete accommodation of the eye. In a most preferred embodiment, the custom accommodating artificial ocular lens (c-AAOL) device according to the present invention visually or optically corrects, protects, or otherwise overcomes any and all visual problems or defects.

The custom accommodating artificial ocular lens (c-AAOL) device according to the present invention is manufactured or designed after thoroughly examining, measuring and mapping the patient's eye or eye vision. This information is compiled and then processed to custom manufacture or make the custom accommodating artificial ocular lens (c-AAOL) device for the particular patient. For example, the patient's eye is evaluated for power correction, astigmatism correction, abnormal surface correction, abnormal refractive correction, abnormal tissue correction, and disease correction. For example, abnormal surface profiles or blemishes on the front and/or back surface and/or within the cornea and lens (e.g. natural lens or IOL) are analyzed by wavefront mapping and/or topography of the eye, measuring the internal dimensions of the eye, including cornea, anterior chamber, iris, pupil, posterior chamber, capsular bag, retina, to determine the condition of the eye.

The information from the eye examination, measurements and mapping are processed through a mathematical formula or algorithm embodied in a computer program to calculate the biological, chemical, and physical parameters or characteristics of the custom accommodating artificial ocular lens (c-AAOL) device to be manufactured or made. Specifically, the exact lens size, lens thickness, lens length, lens width, optic location, optic shape, material, material physical properties, material chemistry, material surface chemistry, material refractive index, material hardness, material resilience, material elasticity, material finish, front lens surface conformation, back lens surface conformation, lens curvature, and other processing factors or parameters are determined, and then transformed into machine language for controlling highly precise and accurate computer operated manufacturing equipment (e.g. digitally operated tools) such as lathes, mills, grinding machinery, laser, surface finishing machinery, or any other type of machinery or processes that can be computer operated and controlled for cutting the custom accommodating artificial ocular lens (c-AAOL) device or for cutting a mold for making the custom accommodating artificial ocular lens (c-AAOL) device A preferred embodiment of the custom accommodating artificial ocular lens (c-AAOL) device according to the present invention adjusts the overall or macro power of the eye and corrects the astigmatism of the eye. Specifically, the lens optic portion is provided with 1) a lens optic portion for changing the overall or macro power of the eye; and 2) a lens optic portion for correction astigmatism of the eye. For example, the power correction of the lens optic portion can be obtained by cutting or contouring the main overall or macro shape and thickness of the lens optic portion and/or the lens optic portion can be made multi-focal. The lens optic portion can be multi-focal by providing one or both surfaces of the lens optic portion with a multi-focal surface(s). The astigmatic correction of the lens optic portion can be obtained by providing a toric lens optic portion and/or by tilting (i.e. fixed or permanent tilt and/or varying tilting) of the lens optic portion. For example, one or both surfaces of the lens optic portion is provided with toric surfaces.

A more preferred embodiment of the custom accommodating artificial ocular lens (c-AAOL) device according to the present invention adjusts the power of the eye, corrects the astigmatism of the eye, and corrects the fine or micro optics of eye based on wavefront analysis and mapping of the eye. For example, the power correction of the lens optic portion can be obtained by cutting or contouring the main overall or macro shape and thickness of the lens optic portion and/or the lens optic portion can be made multi-focal refractive and/or diffractive. The astigmatic correction of the lens optic portion can be obtained by providing a toric and/or diffractive lens optic portion. For example, one or both surfaces of the lens optic portion can be made with toric surfaces. Further; the lens optic portion can be made to provide point-to-point optical modification, adjustment, change or fine tuning of the structure and/or shape of the lens optic portion throughout the three dimensions (3-D) of the lens optic portion to micro fine tune or make micro modifications, micro adjustments or micro changes to the lens optic portion on a micro basis to eliminate any and all optical aberrations and provide for full wavefront optical corrections.

A most preferred embodiment of the custom accommodating artificial ocular lens (c-AAOL) device according to the present invention includes macro power adjustment, micro power adjustment, multi-focal, toric, and wavefront optics adjustment or correction on one or both sides of the accommodating (i.e. moving) lens optic, and/or within the interior of the accommodating (i.e. moving) lens optic portion.

The accommodating artificial ocular lens (AAOL) device according to the present invention is preferably custom made to correct any and all vision or optical problems or defects of the eye, including power correction, astigmatism correction, corneal surface and interior aberrations, lens surface and interior aberrations (natural or replacement lens, IOL), and other optical aberrations from other eye structure, eye aqueous and/or eye vitreous. In order to provided a custom accommodating artificial ocular lens (c-AAOL) device, it is required that the vision or optical defects of the eye are carefully measured, for example, by a visual field analyzer, slit lamp, biomicroscope and opthalmoscope. The goal is to provide an accurate and precise "eye assessment" to correct macro vision or optical defects or problems, and micro vision or optical defects or problems such as higher-order aberrations. The wavefront analysis based on adaptic measures of light deviations and aberrations can be measured to 0.01 microns ($\mu$m) equivalent to approximately 0.001 diopter (D) adjustment by root mean square deviations (RMS units). Standard refraction methods are used to measure macro visual or optical defects or problems such as low-order aberrations (second-order sphere or defocus and cylinder in 0.25 diopter (D) steps. Up to twenty percent (20%) of the higher-order aberrations come from the corneal, aqueous, lens, and/or vitreous accounting for numerous changes in the indices of refraction of light rays moving through the eye.

The higher-order aberrations require measuring equipment exceeding standard or conventional refractive measuring instruments. The higher-order aberrations include coma (third-order), trefoil (third-order), spherical aberrations and quadra foil (fourth-order), and irregular astigmatism (fifth-order to eighth-order). These higher-order aberrations provide refractive abnormalities well below 0.25 diopter (D unit) translating to three microns ($\mu$m) of tissue change within the eye. The wavefront analysis and mapping desired utilizes adaptive optics for measuring root mean square deviation (RMS) using measuring sensors such as a deformable "lenslent" systems to calculate RMS coefficients. The RMS coefficients are then converted into a polynomial pyramid (e.g. Zerneky Pyramid). The three dimensional (3-D) models or two dimensional (2-D) color maps indicate lower and higher order aberrations of the eye. The Zerneky polynomial measure aberrations up to the eleventh (11th) order, and can virtually analyze a hundred percent (100%) of the aberrations of the eye. Above the sixth (6th) order, only noise is created. Point spread functions (PSF) are used to measure and assess higher-orders aberrations in the human vision. These higher-order aberrations include distortions, haloes, tails, and/or double (overlapping) images.

The custom accommodating artificial ocular lens (c-AAOL) device can be made by selecting a material capable of being machined, and then cutting or contouring the front and back surface of the lens optic portion from a blank using a digital lathe, digital mill, laser, or by use of microlithography and/or etching to form or make lens structure or markings. For materials that can be molded, the lens optic portion can be made by machining and polishing a mold cavity, and then molding the lens from a desired material. In a preferred embodiment, the lens mold utilizes a replaceable insert, in particular a replaceable molding pin for molding the lens optic portion of the lens. In this manner, the molding pin can be replaced each time a lens is molded to make a one of a kind custom lens optic portion for a particular patient. The remaining portions of the mold (e.g. to mold plate haptic portion) can be of a standard size and shape, and otherwise not customized.

The molding pin for molding the lens optic portion of the custom accommodating artificial ocular lens (c-AAOL) device can be made by machining the molding pin surface thereof, and then highly polishing the molding pin surface. In a more preferred embodiment, the surface of the molding pin is machined, and then treated to provide a thin metal oxide layer thermally and/or electromagnetically deposited (e.g. vacuum deposited) to eliminate the need for the step of polishing the surface. Specifically, the molding pin is made of a copper/nickel alloy and the molding surface is diamond machined, and then a layer of corundum or aluminum oxide (e.g. sapphire, ruby, diamond (carboneaous)) is vacuum deposited on the molding surface to increase smoothness and durability thereof. The layer is preferably in the thickness range of fifty (50) to four-hundred (400) angstroms (Å).

The custom accommodating artificial ocular lens (c-AAOL) device refractive correction lens according to the present invention can also be used to correct vision or optical defects or problems from prior surgical procedures and/or implants (e.g. after LASIK refractive correction of the cornea and/or after implantation of an IOL).

BRIEF DESCRIPTION OF THE DRAWINGS

FIG. 43A is a broken away top planar view of the front side of a lens optic portion of a preferred embodiment of the accommodating artificial ocular lens (AAOL) device according to the present invention having a bifocal front surface portion.

FIG. 43B is a broken away bottom planar view of the back side of the lens optic portion, as shown in FIG. 43A.

FIG. 44 is a top planar view of another embodiment of the accommodating artificial ocular lens (AAOL) device according to the present invention having an oval or elipse shaped lens haptic portion.

FIG. 45 is a top planar view of a further embodiment of the accommodating artificial ocular lens (AAOL) device according to the present invention having an oblong-shaped lens haptic portion.

FIG. 46 is a top planar view of another further embodiment of the accommodating artificial ocular lens (AAOL) device having a rectangular-shaped lens haptic portion with round-shaped ends.

FIG. 47 is a top planar view of an even further embodiment of the accommodating artificial ocular lens (AAOL) device according to the present invention having a spheric-shaped lens haptic portion with square ends.

FIG. 53 is a top planar view of an even further embodiment of the accommodating artificial ocular lens (AAOL) device according to the present invention.

FIG. 54 is a side elevational view of the embodiment shown in FIG. 53.

FIG. 55 is a perspective view of another even further embodiment of the accommodating ocular lens (AAOL) device according to the present invention.

FIG. 56 is a side elevational view of the embodiment shown in FIG. 55.

DETAILED DESCRIPTION OF PREFERRED EMBODIMENTS

A preferred embodiment of a deformable accommodating artificial ocular lens (AAOL) device 10 according to the present invention is shown in FIGS. 1 to 4.

Figure 2:
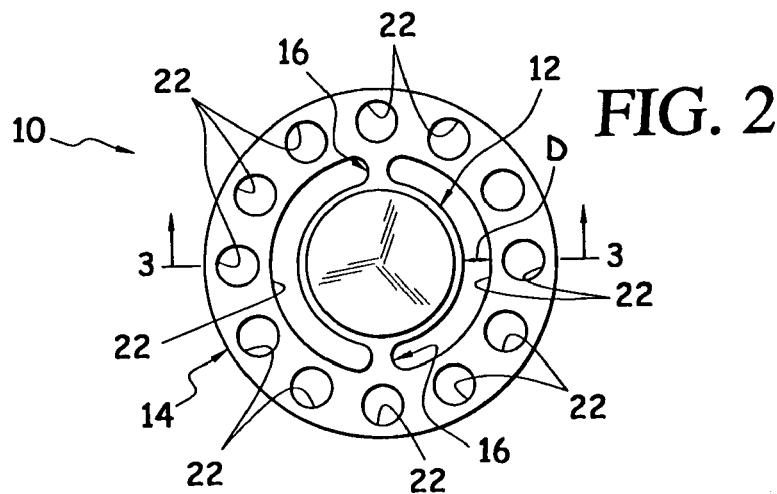
FIG. 2 is a top planar view of the deformable accommodating artificial ocular lens (AAOL) device, as shown in FIG. 1.
Figure 3:
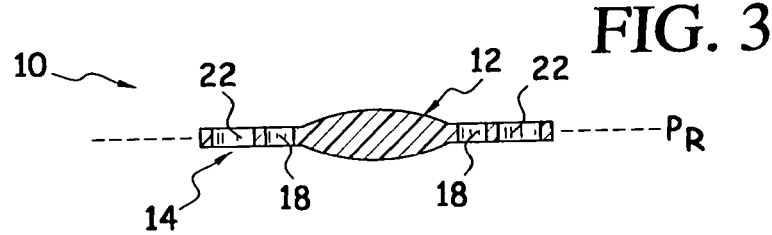
FIG. 3 is a cross-sectional view of the deformable accommodating artificial ocular lens (AAOL) device, as indicated in FIG. 2, in an unstressed condition.
Figure 4:
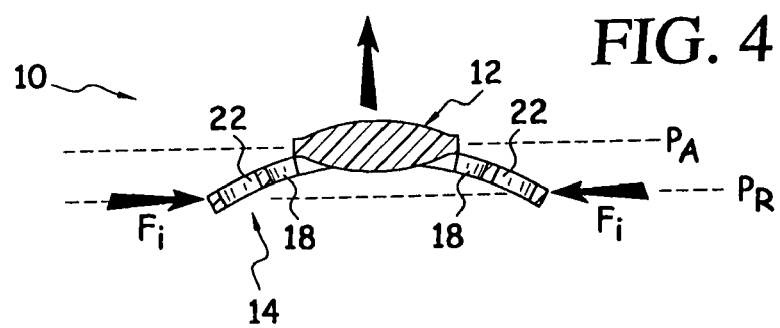
FIG. 4 is a cross-sectional view, as shown in FIG. 3, when the accommodating artificial ocular lens (AAOL) device is in a stressed condition.

The deformable accommodating artificial ocular lens (AAOL) device 10 includes a lens optic portion 12 and a lens plate haptic portion 14. The lens optic portion 12 is connected to the lens plate haptic portion 14 by a pair of flexible or resilient lens arm portions 16, 16, as shown in FIG. 2. A pair of partial circular-shaped lens openings 18, 18 separate the lens optic portion 12 from the lens plate haptic portion 14, as shown in FIG. 2, by a predetermined distance D. In this manner, the lens optic portion 12 is structurally substantially independent of lens plate haptic portion 18, except at the two (2) points of connection provided by the resilient or flexible lens arm portions 16, 16.

The perimeter of the lens plate haptic portion 14 is provided with a plurality of lens through holes 22 to facilitate adherence of tissue through the lens through holes 22 by tissue located on either side of the perimeter of the lens plate haptic portion 14 connecting together in and through the lens through holes 22. In this manner, once the deformable accommodating artificial ocular lens (AAOL) device 10 has been implanted and the eye has healed, the perimeter of the lens plate haptic portion 14 becomes substantially anchored in place.

In the preferred embodiments shown in FIGS. 1 to 4, the lens optic portion 12, lens plate haptic portion 14 and lens arm portions 16, 16 are made together as a one-piece unitary structure from soft, flexible, resilient, foldable, compressible or deformable polymer material (e.g. by molding or machining a single piece of stock material). The deformable accommodating artificial ocular lens (AAOL) device 10 can be inserted through a small incision (e.g. 2.0 mm or less) through the cornea of the eye in a deformed rolled, folded or otherwise compressed condition by use of forceps or a lens injecting device.

Figure 5:
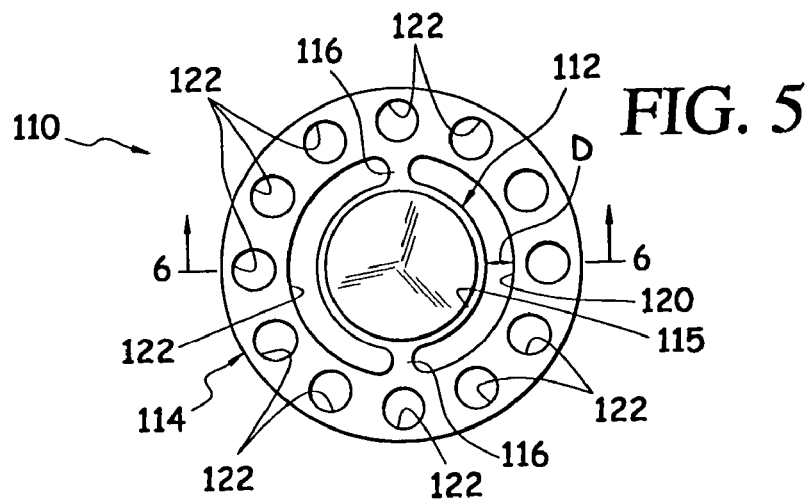
FIG. 5 is a top planar view of another embodiment of the accommodating artificial ocular lens (AAOL) device according to the present invention.
Figure 6:
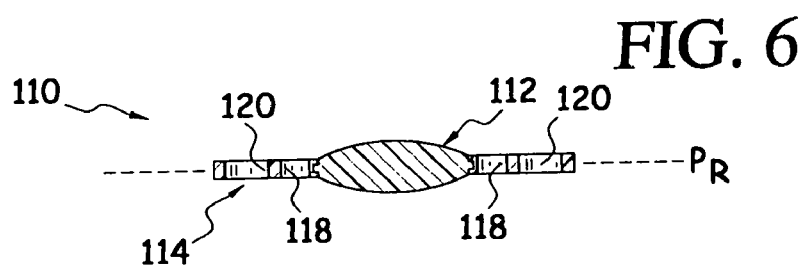
FIG. 6 is a cross-sectional view of the artificial ocular lens (AAOL) device as indicated in FIG. 5.
Figure 7:
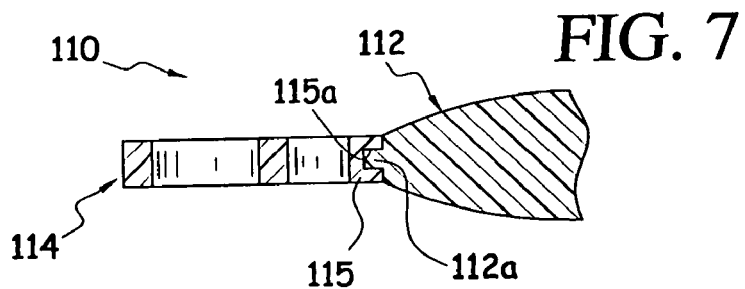
FIG. 7 is a partial broken away detailed cross-sectional view of a portion of the accommodating artificial ocular lens (AAOL) device shown in FIGS. 5 and 6.

Another embodiment of a partially deformable accommodating artificial ocular lens (AAOL) device 110 is shown in FIGS. 5-7.

The partially deformable accommodating artificial ocular lens (AAOL) device 110 includes a lens optic portion 112 and a lens plate haptic portion 114. The lens optic portion 112 is connected to the lens plate haptic portion 114 by a pair of resilient or flexible lens arm portions 116.

In this particular preferred embodiment, the lens optic portion 112 is made out of non-resilient or non-deformable material such as polymethyl methacrylate or hard type polyimide. However, the plate haptic portion 114 is made from a resilient polymer material and the partially deformable accommodating artificial ocular lens (AAOL) device 110 is made from two (2) separate pieces and assembled together to become a single piece accommodating artificial ocular lens (AAOL) device. Further, the accommodating artificial ocular lens (AAOL) device according to the present invention can be made of a material that varies in hardness or stiffness along its length (e.g. harder lens optic portion and softer lens plate haptic portion, or reverse).

The lens plate haptic portion 114 includes a resilient lens carrier or lens receiving portion 115 provided with an inner groove 115a cooperating with a tongue portion 112a of the lens optic portion 112 as shown in FIG. 7. The lens optic portion 112 can be secured in place due to the resilient nature of the lens receiver or lens carrier 115 of the lens plate haptic portion 114 due to its capacity to withstand a certain amount of band stress. Alternatively, or in addition, the tongue portion 112a can be adhered by glue, adhesive, welding or other technique to secure the lens optic portion 112 to the lens receiver or lens carrier 115 of the lens plate haptic portion 114.

The partially deformable accommodating artificial ocular lens (AAOL) device is inserted through a relatively large incision made in the cornea by forceps and then implanted into the capsular bag after cataract lens removal.

Figure 8:
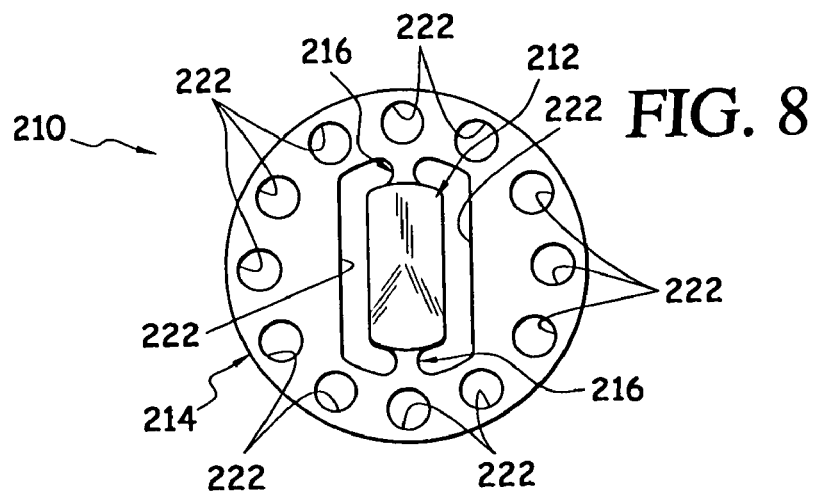
FIG. 8 is a top planar view of another embodiment of an accommodating artificial ocular lens (AAOL) device according to the present invention.

A further embodiment of the accommodating artificial ocular lens (AAOL) device 210 according to the present invention is shown in FIG. 8.

The accommodating artificial ocular lens (AAOL) device 210 includes a substantially rectangular lens optic portion 212 connected to a round-shaped lens plate haptic portion 214 by a pair of flexible or resilient lens arm portions 216, 216. A pair of oblong or partially oval-shaped or arc-shaped lens openings 220, 220 are provided between the lens optic portion 212 and the lens plate haptic portion 214. A plurality of lens through holes 222 are provided to facilitate anchoring of the perimeter of the lens plate haptic portion 214.

Figure 9:
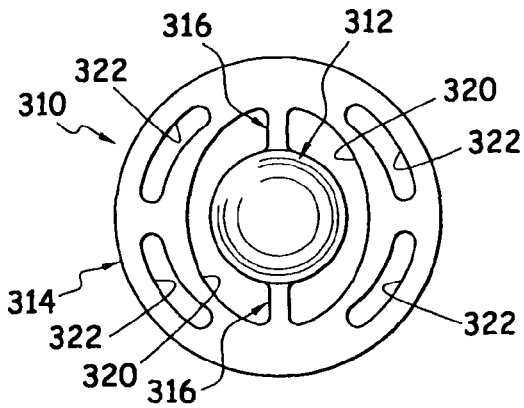
FIG. 9 is a top planar view of another embodiment of an accommodating artificial ocular lens (AAOL) device according to the present invention.

A further embodiment of the accommodating artificial ocular lens (AAOL) device 310 according to the present invention is shown in FIG. 9.

The accommodating artificial ocular lens (AAOL) device 310 includes a substantially round lens optic portion 312 connected to a round-shaped lens plate haptic portion 314 by a pair of flexible or resilient lens arm portions 316, 316. A pair of oblong or partially oval-shaped or arc-shaped lens openings 320, 320 are provided between the lens optic portion 312 and the lens plate haptic portion 314. A plurality of lens through holes 322 are provided to facilitate anchoring of the perimeter of the lens plate haptic portion 314.

Figure 10:
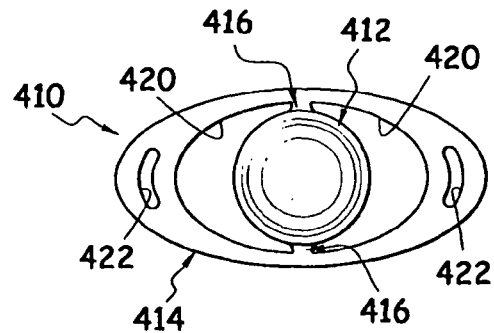
FIG. 10 is a top planar view of another embodiment of an accommodating artificial ocular lens (AAOL) device according to the present invention.

A further embodiment of the accommodating artificial ocular lens (AAOL) device 410 according to the present invention is shown in FIG. 10.

The accommodating artificial ocular lens (AAOL) device 410 includes a substantially round-shaped lens optic portion 412 connected to an oblong-shaped or oval-shaped or arc-shaped lens plate haptic portion 414 by a pair of flexible or resilient lens arm portions 416, 416. A pair of oblong or partial oval-shaped or arc-shaped lens openings 420, 420 are provided between the lens optic portion 412 and the lens plate haptic portion 414. A plurality of lens through holes 422 are provided to facilitate anchoring of the perimeter of the lens plate haptic portion 414.

Figure 11:
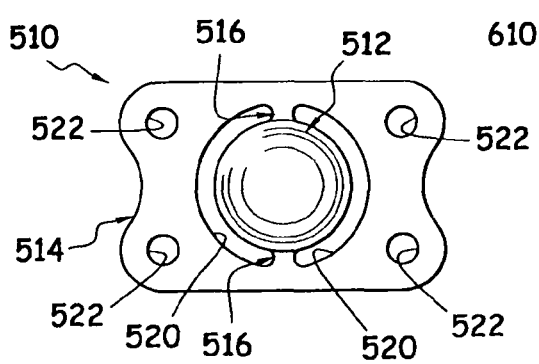
FIG. 11 is a top planar view of another embodiment of an accommodating artificial ocular lens (AAOL) device according to the present invention.

A further embodiment of the accommodating artificial ocular lens (AAOL) device 510 according to the present invention is shown in FIG. 11.

The accommodating artificial ocular lens (AAOL) device 510 includes a round-shaped lens portion 512 connected to a modified oblong-shaped or substantially rectangular-shaped lens plate haptic portion 514 by a pair of flexible or resilient lens arm portions 516, 516. A pair of oblong or partial oval-shaped lens openings 520, 520 are provided between the lens optic portion 512 and the lens plate haptic portion 514. A plurality of lens through holes 522 are provided to facilitate anchoring of the perimeter of the lens plate haptic portion 514.

Figure 12:
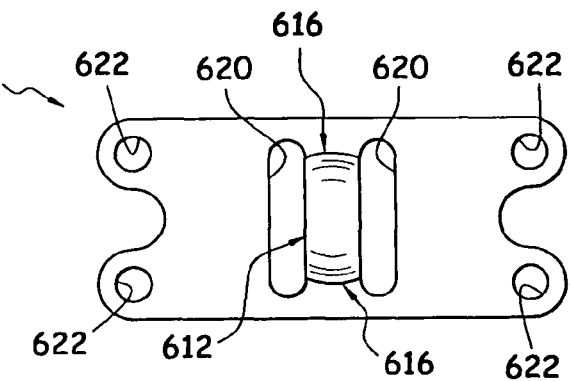
FIG. 12 is a top planar view of another embodiment of an accommodating artificial ocular lens (AAOL) device according to the present invention.

Another embodiment of the accommodating artificial ocular lens (AAOL) device 610 according to the present invention is shown in FIG. 12.

The accommodating artificial ocular lens (AAOL) device 610 includes an elongated lens optic portion 612 connected to an elongated lens plate haptic portion 614 by a pair of flexible or resilient lens arm portions 616, 616. A pair of oblong-shaped or oval-shaped or arc-shaped lens openings 620, 620 are provided between the lens optic portion 612 and the lens plate haptic portion 614. A plurality of lens through holes 622 are provided to facilitate anchoring of the ends of the lens plate haptic portion 614 in the eye.

Figure 13:
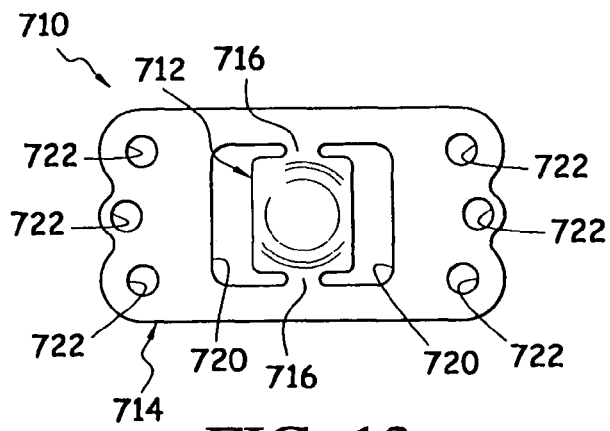
FIG. 13 is a top planar view of another embodiment of an accommodating artificial ocular lens (AAOL) device according to the present invention.

A further embodiment of the accommodating artificial ocular lens (AAOL) device 710 according to the present invention is shown in FIG. 13.

The accommodating artificial ocular lens (AAOL) device 710 includes a rectangular-shaped lens optic portion 712 connected to a rectangular-shaped lens plate haptic portion 714 by a pair of flexible or resilient lens arm portions 716, 716. A pair of rectangular oval-shaped or arc-shaped lens openings 720, 720 are provided between the lens optic portion 712 and the lens plate haptic portion 714. A plurality of lens through holes 722 are provided to facilitate anchoring of the ends of the lens plate haptic portion 714 within the eye.

Figure 14:
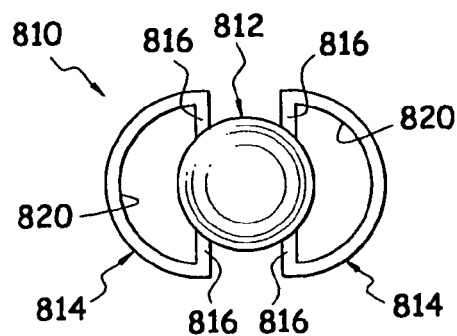
FIG. 14 is a top planar view of another embodiment of an accommodating artificial ocular lens (AAOL) device according to the present invention.

An even further embodiment of the accommodating artificial ocular lens (AAOL) device 810 according to the present invention is shown in FIG. 14.

The accommodating artificial ocular lens (AAOL) device 810 includes a round-shaped lens optic portion 812 connected to a pair of half-circle shaped or arc-shaped lens plate haptic portions 814, 814 each by a pair of flexible or resilient lens arm portions 816, 816. A pair of half-circle shaped or arc-shaped lens openings 820, 820 are provided between the lens optic portion 812 and the lens plate haptic portions 814, 814. In this embodiment, the lens openings 820, 820 also provide the function of lens through holes in previous embodiments to facilitate anchoring the ends of the lens plate haptic portions 814, 814 in the eye.

Figure 15:
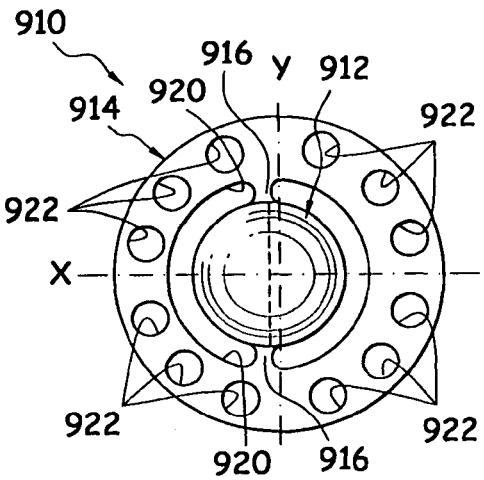
FIG. 15 is a top planar view of another embodiment of an accommodating artificial ocular lens (AAOL) device according to the present invention.

Another embodiment of the accommodating artificial ocular lens (AAOL) device 910 according to the present invention is shown FIG. 15.

The accommodating artificial ocular lens (AAOL) device 910 includes a round-shaped lens optic portion 912 connected to a round-shaped lens plate haptic portion 914 by a pair of flexible or resilient lens arm portions 916, 916. The lens arm portions 916, 916 are approximately the same length. A pair of half circular-shaped or arc-shaped lens openings 920, 920 are provided between the lens optic portion 912 and the lens plate haptic portion 914. A plurality of lens through holes 922 are provided to facilitate anchoring the lens plate haptic portion 914 in the eye. In this embodiment, the lens optic portion 912 is located off-centered along the Y axis making the round-shaped lens plate haptic portion somewhat asymmetrical in shape relative to the X axis.

Figure 16:
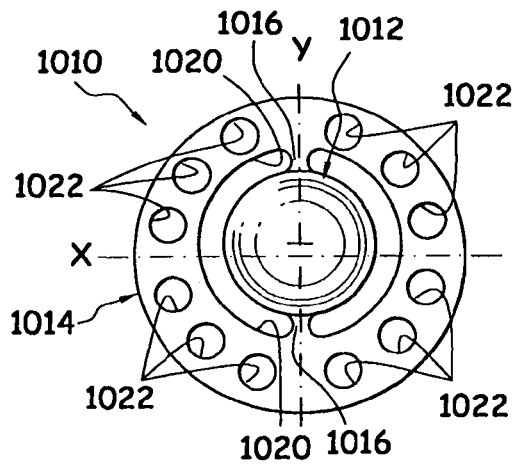
FIG. 16 is a top planar view of a further embodiment of an accommodating artificial ocular lens (AAOL) device according to the present invention.

Another embodiment of the accommodating artificial ocular lens (AAOL) device 1010 according to the present invention is shown in FIG. 16.

The accommodating artificial ocular lens (AAOL) device 1010 includes a round-shaped lens portion 1012 connected to a round-shaped lens plate haptic portion 1014 by a pair of flexible or resilient lens arm portions 1016, 1016. A pair of half circle-shaped lens openings 1020, 1020 are provided between the lens optic portion 1012 and the lens plate haptic portion 1014. A plurality of lens through holes 1022 are provided to facilitate anchoring the perimeter of the lens plate haptic portion 1014 in the eye. In this embodiment, the lens optic portion 1012 is located off-center along the X axis resulting in the lens plate haptic portion 1014 being asymmetrical relative to the Y axis.

Figure 17:
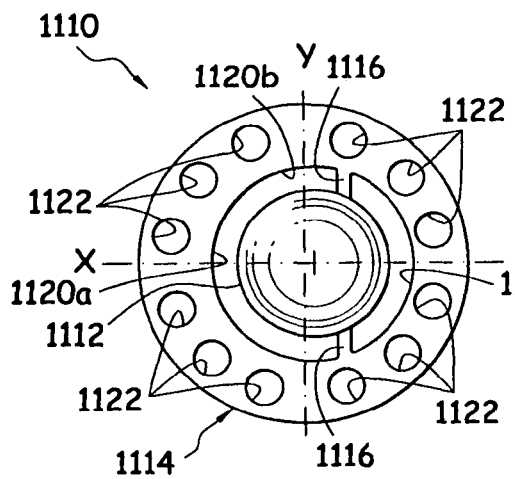
FIG. 17 is a top planar view of a further embodiment of an accommodating artificial ocular lens (AAOL) device according to the present invention.

Another embodiment of the accommodating artificial ocular lens (AAOL) device 1110 according to the present invention is shown in FIG. 17.

The accommodating artificial ocular lens (AAOL) device 1110 includes a round-shaped lens portion 1112 connected to a round-shaped lens plate haptic portion 1114 by a pair of flexible or resilient lens arm portions 1116, 1116. The lens arm portions 1116, 1116 are both located off axis relative to the Y axis. A pair of half circular-shaped lens openings 1120a, 1120b are provided between the lens optic portion 1112 and the lens plate haptic portion 1114. It is to be noted that the lens opening 1120a is larger than the lens opening 1120b. A plurality of lens through holes 1122 are provided to facilitate anchoring of the perimeter of the lens plate haptic portion 1114 in the eye.

Figure 18:
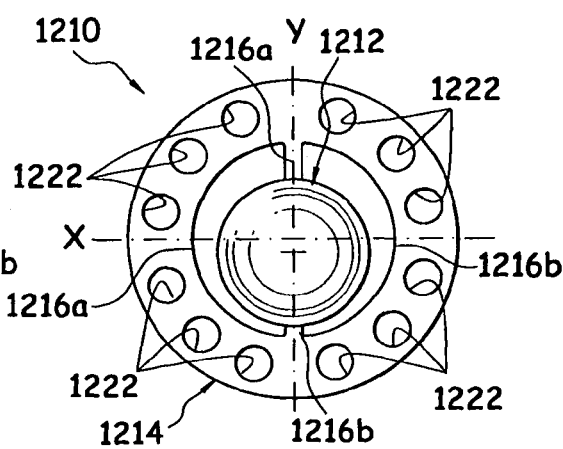
FIG. 18 is a top planar view of another embodiment of an accommodating artificial ocular lens (AAOL) device according to the present invention.

Another embodiment of the accommodating artificial ocular lens (AAOL) device 1210 according to the present invention is shown in FIG. 18.

The accommodating artificial ocular lens (AAOL) device 1210 includes a round-shaped lens optic portion 1212 connected to a round-shaped lens plate haptic portion 1214 by a pair of flexible or resilient lens arm portions 1216a and 1216b. It is to be noted that the lens arm portion 1216a is longer than the lens arm portion 1216b. A pair of asymmetrical half circular-shaped lens openings 1220 are provided between the lens optic portion 1212 and the lens plate haptic portion 1214. A plurality of lens through holes 1222 are provided to facilitate anchoring of the perimeter of the lens plate haptic portion 1214 in the eye.

Figure 19:
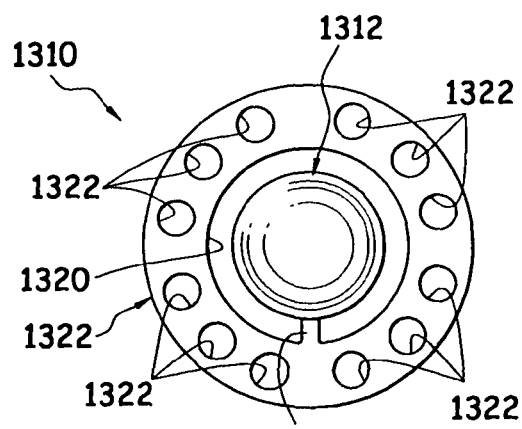
FIG. 19 is a top planar view of a further embodiment of an accommodating artificial ocular lens (AAOL) device according to the present invention.

Another embodiment of the accommodating artificial ocular lens (AAOL) device 1310 according to the present invention is shown in FIG. 19.

The accommodating artificial ocular lens (AAOL) device 1310 includes a round-shaped lens portion 1312 connected to a round-shaped lens plate haptic portion 1314 by a single flexible or resilient lens arm portion 1316. A single circular-shaped lens opening 1320 is provided to separate the lens portion 1312 from the lens plate haptic portion 1314. A plurality of lens through holes 1322 are provided to facilitate anchoring of the perimeter of the lens plate haptic portion 1314 in the eye.

Figure 20:
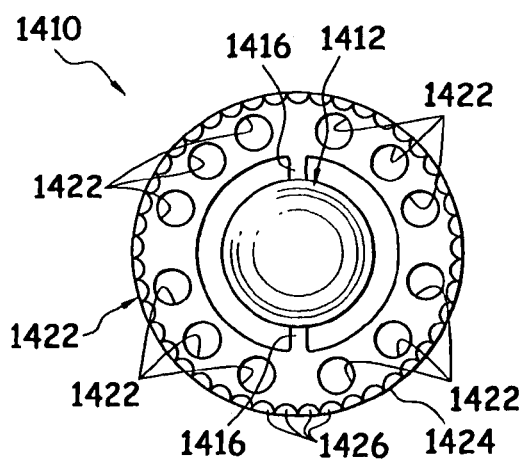
FIG. 20 is a top planar view of a further embodiment of an accommodating artificial ocular lens (AAOL) device according to the present invention.

Another embodiment of the accommodating artificial ocular lens (AAOL) device 1410 according to the present invention is shown in FIG. 20.

The accommodating artificial ocular lens (AAOL) device 1410 includes a round-shaped lens portion 1412 connected to a round-shaped plate haptic portion 1414 by a pair of flexible or resilient lens arm portions 1416, 1416. A pair of half-circle shaped or arc-shaped lens openings 1420, 1420 are provided between the lens optic portion 1412 and the lens plate haptic portion 1414. A plurality of lens through holes 1422 are provided to facilitate anchoring of the perimeter of the lens plate haptic portion 1414 in the eye. In addition, the lens edge 1424 is provided with lens scalloped portions 1426 around the perimeter thereof to facilitate the fibrotic fixation process. Alternatively, or in addition, the lens scalloped portions 1426 can be replaced or augmented with lens edge serrations, notches, protrusions, pins, fingers and/or flaps.

The lens opening in the above-embodiment can be of the same size and/or shape (i.e. symmetrical or mirror-image), or can be of different size and/or shape (i.e. asymmetric) to provide various effects or features customized for a particular patient during accommodation of the lens optic portion.

Figure 21:
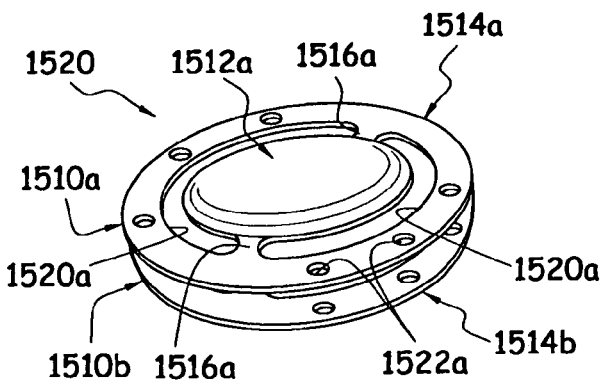
FIG. 21 is a perspective view of an accommodating artificial ocular lens (AAOL) device according to the present invention having double lens optic portions.
Figure 22:
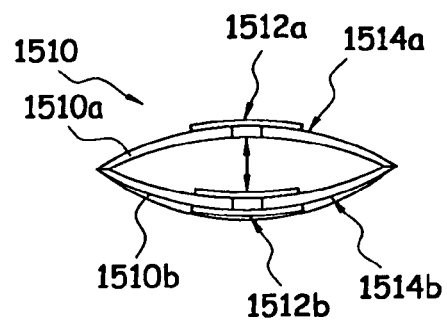
FIG. 22 is a center cross-sectional view of the accommodating artificial ocular lens (AAOL) device shown in FIG. 21.

A double lens optic embodiment of the accommodating artificial ocular lens (AAOL) device 1510 according to the present invention is shown in FIGS. 21 and 22.

The accommodating artificial ocular lens (AAOL) device 1510 includes a front accommodating lens portion 1510a and a back accommodating lens portion 1510b. The lens portion 1510a and the lens portion 1510b are essentially the same configuration except reverse oriented and assembled back-to-back.

The accommodating artificial ocular lens (AAOL) portion 1510a includes a round-shaped lens optic portion 1512a connected to a round-shaped lens plate haptic portion 1514a by a pair of flexible or resilient lens arm portions 1516a, 11516a. A pair of half circular-shaped lens openings 1520a, 1520a are provided between the lens optic portion 1512a and the lens plate haptic portion 1514a. A plurality of lens through holes 1522a are provided to facilitate anchoring of the perimeter of the lens plate haptic portion 1514a in the eye. The accommodating artificial ocular lens (AAOL) portion 1510b is the same or similarly configured to the accommodating artificial ocular lens (AAOL) portion 1510a. As shown in FIG. 22, the outer edges or perimeter of the accommodating artificial ocular lens (AAOL) portions 1510a and 1510b contact or engage each other when implanted in the eye.

The accommodating artificial ocular lens (AAOL) portions 1510a, 1510b can be connected together continuously around the outer perimeter thereof, or can be connected at a number of separate points around the outer perimeter thereof. Further, the accommodating artificial ocular lens (AAOL) portions 1510a, 1510b can be unstressed (i.e. not arched) when assembled together, or can be prestressed (i.e. pre-arched) prior to being assembled together.

A preferred embodiment of the lens plate haptic portion has a length preferably from 8 millimeters to 13 millimeters, a width from 5 to 13 millimeters, and a thickness from 0.05 millimeters to 1 millimeter. The lens opening distance D is preferably 0.20 to 2.0 millimeters. It is important that the ratio of the radial length of the lens plate haptic portion relative to the axial thickness of the lens plate haptic portion is preferably 1.5 to 8 or more, to provide sufficient bowing of the lens plate haptic portion when stressed inwardly by forces applied by the eye.

A variety of different embodiments of the lens optic portion of the accommodating artificial ocular lens (AAOL) device according to the present invention is shown in FIGS. 27A, 27B through FIGS. 43A, 43B.

Figure 27A:
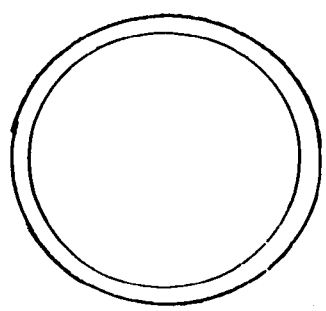
FIG. 27A is a broken away top planar view of the front side of the lens optic portion of the accommodating artificial ocular lens (AAOL) device shown in FIG. 1.
Figure 27B:
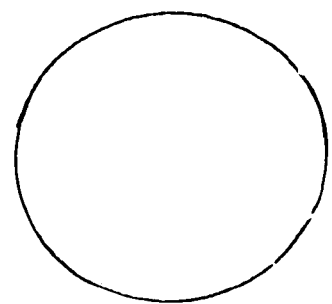
FIG. 27B is a broken away bottom planar view of the back side of the lens optic portion of the accommodating artificial ocular lens (AAOL) device shown in FIG. 1.

In the embodiment shown in FIGS. 27A and B, the front surface of the lens optic portion is provided with front and back optical surface portions configured to provide add or subtract lens power to the eye.

Figure 28A:
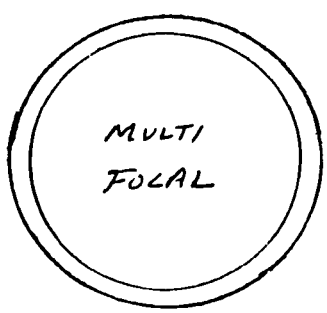
FIG. 28A is a broken away top planar view of the front side of a lens optic portion of a preferred embodiment of the accommodating artificial ocular lens (AAOL) device according to the present invention having a multi-focal front surface portion.
Figure 28B:
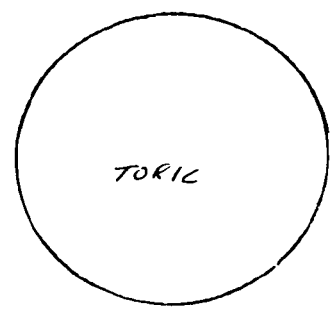
FIG. 28B is a bottom planar view of the back side of the lens optic portion, shown in FIG. 28A, having a toric back surface portion.

In the embodiment shown in FIGS. 28A and B, the front surface of the lens optic portion is provided with a multi-focal front surface portion and the back side of the lens optic portion is provided with a toric back surface portion.

Figure 29A:
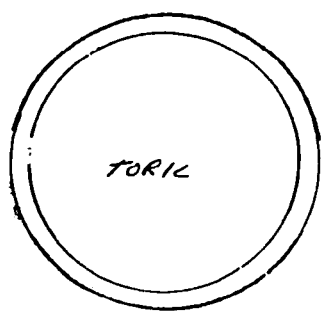
FIG. 29A is a broken away top planar view of the front side of a lens optic portion of a preferred embodiment of the accommodating artificial ocular lens (AAOL) device according to the present invention having a toric front surface portion.
Figure 29B:
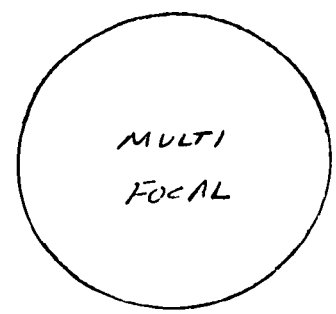
FIG. 29B is a broken away bottom planar view of the back side of the lens optic portion, as shown in FIG. 29A, having a multi-focal back surface portion.

In the embodiment shown in FIGS. 29A and B, the front side of the lens optic portion is provided with a toric front surface portion and the back side of the lens optic portion is provided with a multi-focal back surface portion.

Figure 30A:
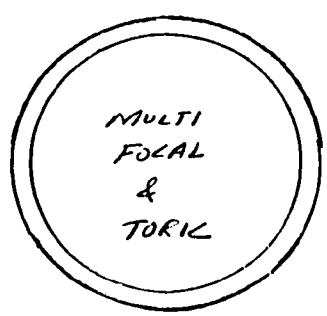
FIG. 30A is a broken away top planar view of the front side of a lens optic portion of a preferred embodiment of the accommodating artificial ocular lens (AAOL) device according to the present invention having both a multi-focal and toric front surface portion.
Figure 30B:
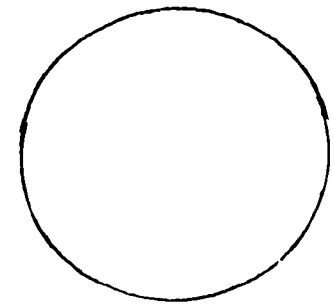
FIG. 30B is a broken away bottom planar view of the back side of the lens optic portion, as shown in FIG. 30A.

In the embodiment shown in FIGS. 30A and B, the front side of the lens optic portion is provided with a both a multi-focal and toric front surface portion and the back side of the lens optic portion is provided with a optical back surface portion.

Figure 31A:
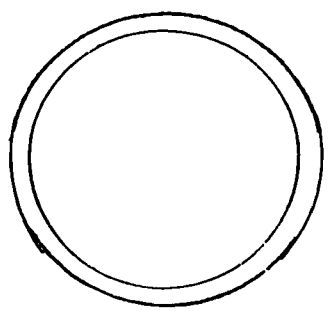
FIG. 31A is a broken away top planar view of the front side of a lens optic portion of a preferred embodiment of the accommodating artificial ocular lens (AAOL) device according to the present invention.
Figure 31B:
FIG. 31B is a broken away bottom planar view of the back side of the lens optic portion, as shown in FIG. 31A, having both a multi-focal and toric back surface portion.

In the embodiment shown in FIGS. 31A and B, the front side of the lens optic portion is provided with an optical front surface portion and the back side of the lens optic portion is provided with both multi-focal and toric back surface portions.

Figure 32A:
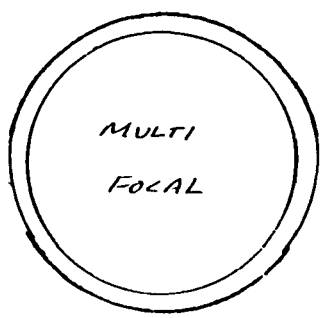
FIG. 32A is a broken away top planar view of the front side of a lens optic portion of a preferred embodiment of the accommodating artificial ocular lens (AAOL) device according to the present invention having a multi-focal front surface portion.
Figure 32B:
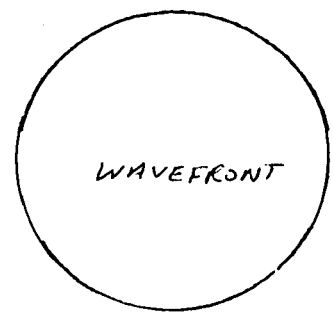
FIG. 32B is a broken away bottom planar view of the back side of the lens optic portion, as shown in FIG. 32A, having a wavefront back surface portion.

In the embodiment shown in FIGS. 32A and B, the front side of the lens optic portion is provided with a multi-focal surface portion and the back side of the lens optic portion is provided with a wavefront back surface portion.

Figure 33A:
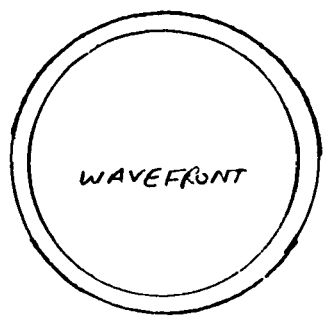
FIG. 33A is a broken away top planar view of the front side of a lens optic portion of a preferred embodiment of the accommodating artificial ocular lens (AAOL) device according to the present invention having a wavefront front surface portion.
Figure 33B:
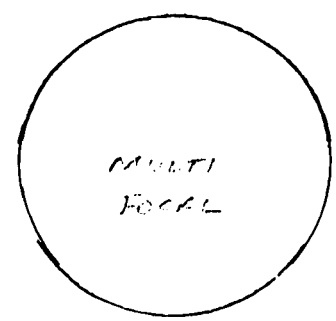
FIG. 33B is a broken away bottom planar view of the back side of the lens optic portion, as shown in FIG. 33A, having a multi-focal back surface portion.

In the embodiment shown in FIGS. 33A and B, the front side of the lens optic portion is provided with a wavefront front surface portion and the back side of the lens optic portion is provided with a multi-focal back surface portion.

Figure 34A:
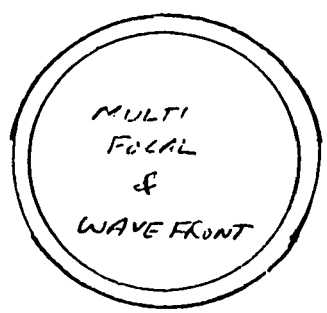
FIG. 34A is a broken away top planar view of the front side of a lens optic portion of a preferred embodiment of the accommodating artificial ocular lens (AAOL) device according to the present invention having both a multi-focal and wavefront front surface portion.
Figure 34B:
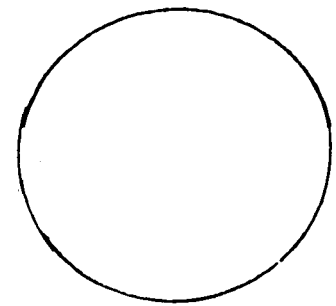
FIG. 34B is a broken away bottom planar view of the back side of the lens optic portion, as shown in FIG. 34A.

In the embodiment shown in FIGS. 34A and B, the front side of the lens optic portion is provided with both a multi-focal and wavefront front surface portion and the back side of the lens optic portion is provided with a optical back surface portion.

Figure 35A:
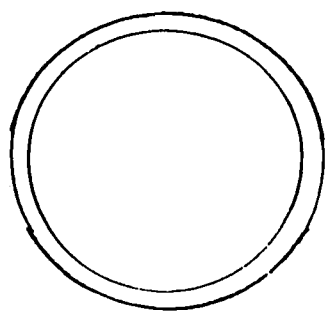
FIG. 35A is a broken away top planar view of the front side of a lens optic portion of a preferred embodiment of the accommodating artificial ocular lens (AAOL) device according to the present invention.
Figure 35B:
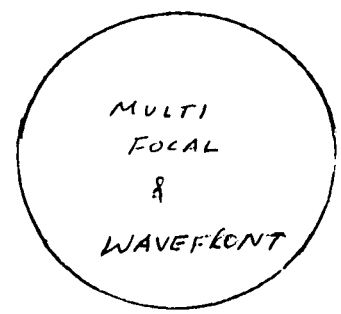
FIG. 35B is a broken away bottom planar view of the back side of the lens optic portion, as shown in FIG. 35A, having both a multi-focal and wavefront back surface portion.

In the embodiment shown in FIGS. 35A and B, the front side of the lens optic portion is provided with an optical front surface portion and the back side of the lens optic portion is provided with both a multi-focal and wavefront back surface portion.

Figure 36A:
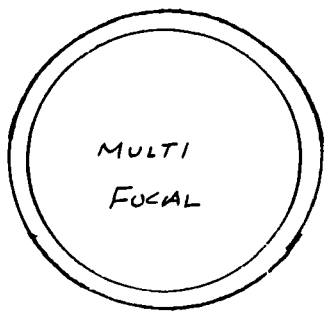
FIG. 36A is a broken away top planar view of the front side of a lens optic portion of a preferred embodiment of the accommodating artificial ocular lens (AAOL) device according to the present invention having a multi-focal front surface portion.
Figure 36B:
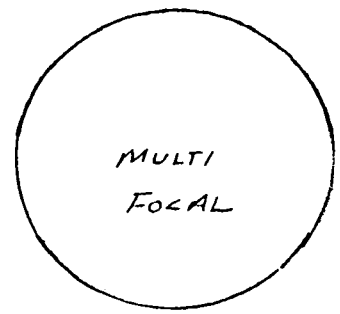
FIG. 36B is a broken away bottom planar view of the back side of the lens optic portion, as shown in FIG. 36A, having a multi-focal back surface portion.

In the embodiment shown in FIGS. 36A and B, the front side of the lens optic portion is provided with a multi-focal front surface portion and the back side of the lens optic portion is provided with a multi-focal back surface portion.

Figure 37A:
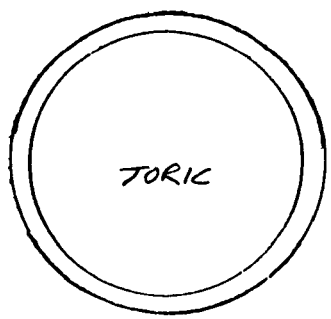
FIG. 37A is a broken away top planar view of the front side of a lens optic portion of a preferred embodiment of the accommodating artificial ocular lens (AAOL) device according to the present invention having a toric front surface portion.
Figure 37B:
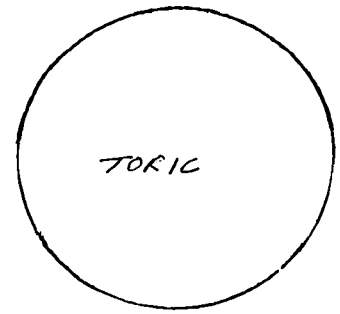
FIG. 37B is a broken away bottom planar view of the back side of the lens optic portion, as shown in FIG. 37A, having a toric back surface portion.

In the embodiment shown in FIGS. 37A and B, the front side of the lens optic portion is provided with a toric front surface portion and the back side of the lens optic portion is provided with a toric back surface portion.

Figure 38A:
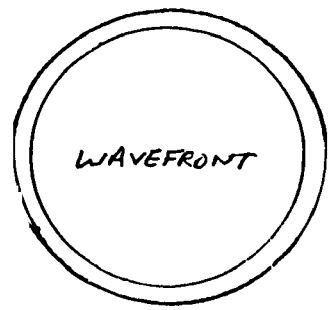
FIG. 38A is a broken away top planar view of the front side of a lens optic portion of a preferred embodiment of the accommodating artificial ocular lens (AAOL) device according to the present invention having a wavefront front surface portion.
Figure 38B:
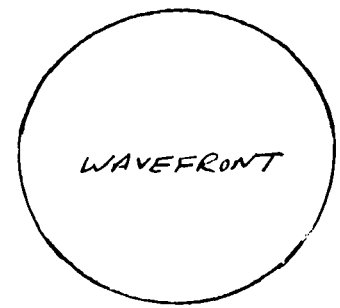
FIG. 38B is a broken away bottom planar view of the back side of the lens optic portion, as shown in FIG. 38A, having a wavefront back surface portion.

In the embodiment shown in FIGS. 38A and B, the front side of the lens optic portion is provided with a wavefront front surface portion and the back side is provided with a wavefront back surface portion.

Figure 39A:
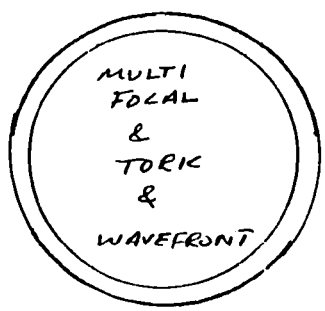
FIG. 39A is a broken away top planar view of the front side of a lens optic portion of a preferred embodiment of the accommodating artificial ocular lens (AAOL) device according to the present invention having a combined multi-focal, toric, and wavefront front surface portion.
Figure 39B:
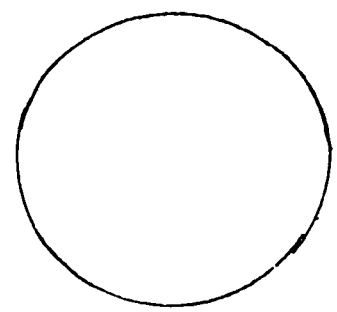
FIG. 39B is a broken away bottom planar view of the back side of the lens optic portion, as shown in FIG. 10A.

In the embodiment shown in FIGS. 39A and B, the front side of the lens optic portion is provided with combined multi-focal and toric and wavefront front surface portion and the back side of the lens optic is provided with an optical back surface portion.

Figure 40A:
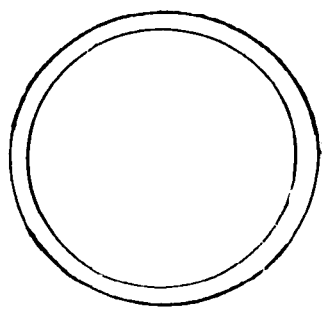
FIG. 40A is a broken away top planar view of the front side of a lens optic portion of a preferred embodiment of the accommodating artificial ocular lens (AAOL) device according to the present invention.
Figure 40B:
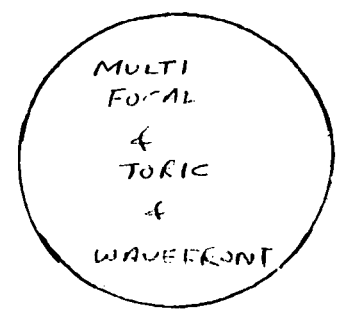
FIG. 40B is a broken away bottom planar view of the back side of the lens optic portion, as shown in FIG. 40A, having a combined multi-focal, toric, and wavefront front surface portion.

In the embodiment shown in FIGS. 40A and B, the front side of the lens optic portion is provided with an optical front surface portion and the back side of the lens optic portion is provided with a combined multi-focal and toric and wavefront surface portion.

Figure 41A:
FIG. 41A is a broken away top planar view of the front side of a lens optic portion of a preferred embodiment of the accommodating artificial ocular lens (AAOL) device according to the present invention having a combined multi-focal, toric, and wavefront front surface portion.
Figure 41B:
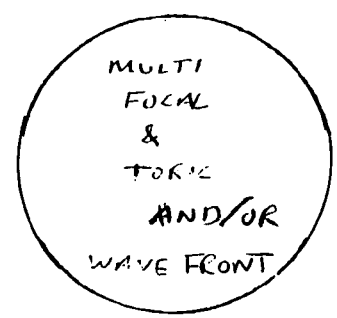
FIG. 41B is a broken away bottom planar view of the back side of the lens optic portion, as shown in FIG. 41A, having a combined multi-focal, toric, and wavefront back surface portion.

In the embodiment shown in FIGS. 41A and B, the front side of the lens optic portion is provided with at least two (2) of a multi-focal, toric and/or wavefront surface portion and the back side of the lens optic portion is provided with at least two (2) of a multi-focal, toric and wavefront surface portion.

Figure 42A:
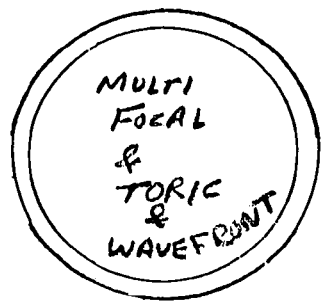
FIG. 42A is a broken away top planar view of the front side of a lens optic portion of a preferred embodiment of the accommodating artificial ocular lens (AAOL) device according to the present invention.
Figure 42B:
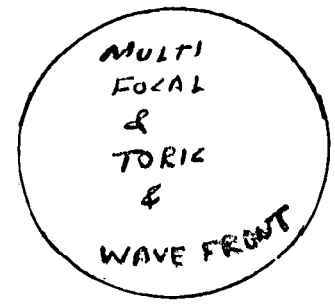
FIG. 42B is a broken away bottom planar view of the back side of the lens optic portion, as shown in FIG. 42A.

In the embodiment shown in FIGS. 42A and B, the front side of the lens optic portion is provided with a multi-focal and toric and wavefront front surface portion and the back side of the lens optic portion is provided with a multi-focal and toric and wavefront back surface portion.

In the embodiment shown in FIGS. 43A and B, the front side of the lens optic portion 1612 is provided with a two (2) multi-focal and/or diffractive lens zones or surfaces 1612a, 1612b, including a circular-shaped center multi-focal and/or diffractive lens surface 1612a and a concentric outer ring-shaped multi-focal and/or diffractive lens surface 1612b on the front surface thereof. Optionally, one multi-focal and/or diffractive lens surface or zone can be provided on one (1) side of the lens optic 1612 and the other multi-focal and/or diffractive lens zone can be provide on the opposite side. As a further option, multiple multi-focal and/or diffractive lens surfaces or zones can be provided on both the front surface and back surface of the lens optic 1612. In another embodiment, the lens optic portion 1612 is provided with three (3) multi-focal and/or diffractive lens zones or surfaces 1612a, 1612b, 1612c.

For a presbyopic embodiment of the accommodating artificial ocular lens (AAOL) device 1612 according to the present invention, for example, the central additions for the lens surface 1601a should be +3.00 diopters (D). Similar but slightly different refractive correction lenses 1612 can be made for early presbyopes and late presbyopes. For example, for early presbyopes, lens surface 1612a should be +0.5 diopters (D) and for late presbyopes, lens surface 1612a should be +3.0 diopters (D). The central lens surface 1612a should be one (1) to four (4) millimeters (mm).

Again, the accommodating artificial ocular lens (AAOL) device 1612 can be provided with a third multi-focal surface or zone 1612c to provide a trifocal (e.g. −1, 0, +1). For example, three (3) object distances, the type of structure (e.g. sine wave, trapezoid and/or rectangle), and the lens material can be specified for making the trifocal embodiment. In other embodiment, more than three (3) multi-focal surfaces or zone (e.g. concentric, symmetric, asymmetric, matrix arrangements of surfaces or zones) can be used for particular applications or custom made for a particular eye. Alternatively, lithography can be used to print marks or a pattern on one or both surfaces of the lens (e.g. grid, rings, matrix) to cause light diffraction to make a diffractive lens optic, or lithography combined with etching (e.g. lens mold surface) can be used to make nanometer to angstrom dimension profiles, protrusions, patterns, contours on lens surfaces to provide multi-focal and/or defractive lens surfaces.

A variety of embodiments of the accommodating artificial ocular lens (AAOL) device having different lens haptic shapes are shown in FIGS. 44-47.

Figure 1:
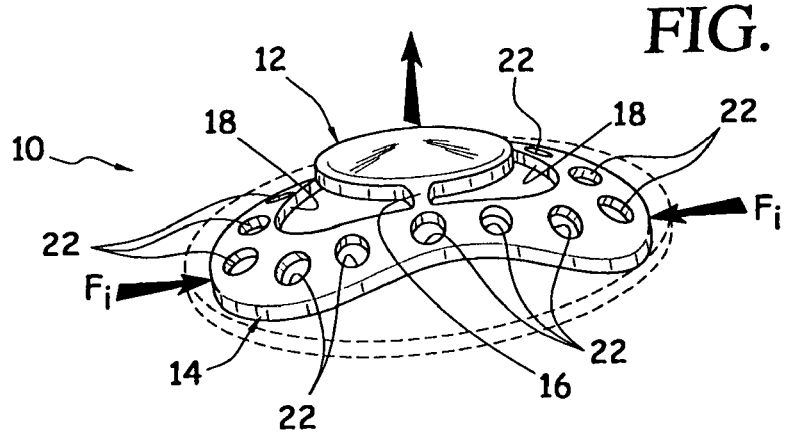
FIG. 1 is a perspective view of a deformable accommodating artificial ocular lens (AAOL) device according to the present invention shown under a stressed condition providing forward accommodation of the lens portion along the center focal axis of the eye.

In the embodiments shown in FIG. 44, the lens haptic portion 1714 is oval-shaped or spherical-shaped versus the circular-shaped configuration shown in the embodiment of FIG. 1.

In the embodiment shown in FIG. 45, the lens haptic portion 1814 is oblong-shaped. Specifically, the lens haptic portion 1814 has straight side portions 1814a and circular-shaped end portions 1814b.

In the embodiments shown in FIG. 46, the lens haptic portion 1914 has longer straight portions 1914a (compared with the embodiment of FIG. 45) and circular-shaped end portions 1914b.

In the embodiments shown in FIG. 47, the lens haptic portion 2014 has oval-shaped or elliptical-shaped side portion 2014a and straight or square end portions 2014b.

Figure 48:
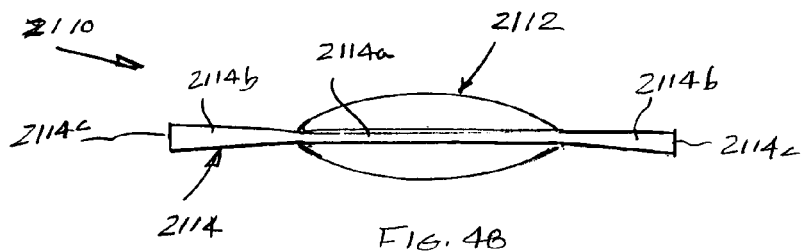
FIG. 48 is a side elevational view of another accommodating artificial ocular lens (AAOL) device having a tapering lens haptic portion.
Figure 49:
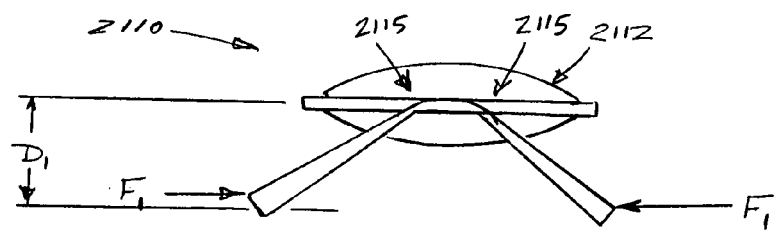
FIG. 49 is a side elevational view of the embodiment shown in FIG. 48, in a stressed and bowed condition.

In the embodiment shown in FIGS. 48 and 49, the accommodating artificial ocular lens (AAOL) device 2110 includes a tapering lens haptic portion 2114. Specifically, the thickness of the center lens haptic portion 2114a is substantially uniform and thin, and then begins to taper and thicken in an outwardly direction to define tapered lens haptic portions 2114b. The tapering and thickening of the lens haptic end portions 2114b strengthens the tapered lens haptic portions 2114b towards the lens haptic portion ends 2114a thereof to prevent bending along the length of the tapered lens haptic portions 2114b. In this manner, as shown in FIG. 49, the tapered lens haptic portions 2114b bend sharply at points 2115 (i.e. bending force is concentrated at positions 2114b). This arrangement significantly increases the accommodating or throw distance $D_1$ of the lens optic 2112 compared with an embodiment having a uniform thickness lens haptic portion.

Figure 50:
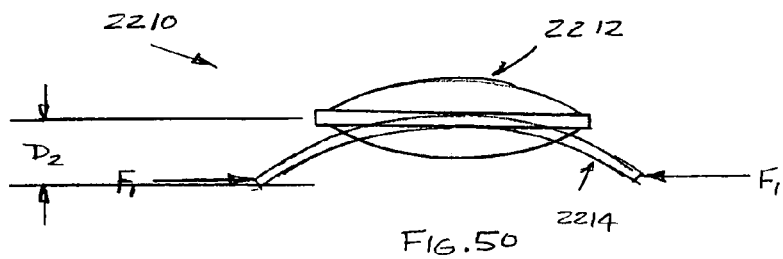
FIG. 50 is a side elevational view of a further embodiment of the accommodating artificial ocular lens (AAOL) device according to the present invention for comparing with the embodiment of FIG. 48.

To further illustrate this effect, a comparison embodiment of the accommodating artificial ocular lens (AAOL) device 2210 is shown in FIG. 50 having a uniform thickness lens haptic portion 2214. In this embodiment, the lens haptic portion 2214 bends uniformly from end-to-end (i.e. uniform curvature along length thereof) significantly reducing the accommodating or throw distance $D_2$ compared with $D_1$ of the accommodating artificial ocular lens (AAOL) device 2110. Thus, the tapering of the lens haptic portion provides for a greater accommodating or throw distance for the same amount of the force $F_1$ being exerted inwardly on the ends of the lens haptic portion.

Figure 51:
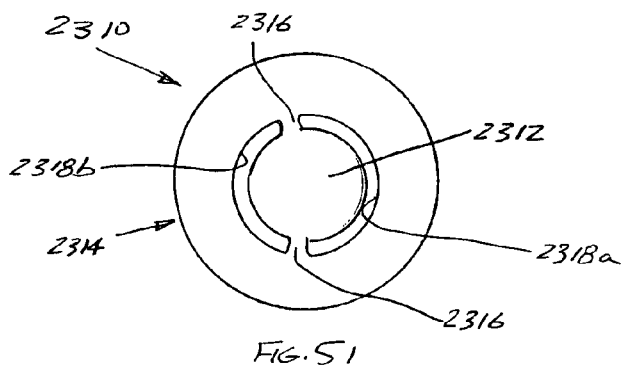
FIG. 51 is a top planar view of another further embodiment of the accommodating artificial ocular lens (AAOL) device according to the present invention.
Figure 52:
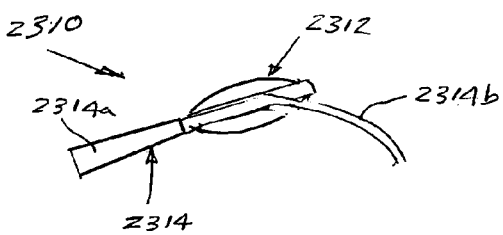
FIG. 52 is a side elevational view of the embodiment shown in FIG. 51.

In the embodiment of the accommodating artificial ocular lens (AAOL) device 2310 shown in FIGS. 51 and 52, the lens optic portion 2312 is progressively tilted as the lens haptic portion 2314 is further bowed. The tilting of the lens optic portion 2312 increases to the optical power of the lens optic portion 2312. To provide tilting of the lens optic portion 2312, the circular-shaped lens openings 2318a, 2318b are made asymmetric in size and/or shape. Further, one side of the lens haptic portion 2314 can be made thicker and/or tapered verses the other side. Specifically, the left lens haptic portion 2314a tapers in thickness outwardly from the lens optic portion 2312 while the right lens haptic portion 2314b remains uniform and thin. In this manner when inwardly force is applied to the ends of the lens haptic protion 2314, the left lens haptic portion 2314a does not bend while the right lens haptic portion 2314b significantly bends causing the lens optic 2312 to progressively bow. The lens haptic portion 2314 can be designed to provide a linear progressive tilting of the lens optic portion 2312, or an exponential progressive tilting of the lens optic portion 2312 relative to the magnitude of the inwardly force applied to the ends of the lens haptic portion 2314 (or relative to the degree of bowing of the lens haptic portion 2314).

In the embodiment shown in FIGS. 53 and 54, the accommodating artificial ocular lens (AAOL) device 2410 is configured to laterally shift the center of the lens optic portion 2412 upon application of inwardly force applied to the ends of the lens haptic portion 2414. For example, the center of the lens optic 2412 is offset from the center of the lens haptic portion 2414, as shown in FIG. 53, when the accommodating artificial ocular lens (AAOL) device 2410 is in an unstressed condition. Further, the left lens haptic portion 2414a is tapered in thickness to prevent bending while the right lens haptic portion 2414b is uniform and thin in thickness. When inwardly force is applied to the ends of the lens haptic portion 2414, the center of the lens optic 2412 shifts to the left by a distance $\Delta_C$ while the lens optic portion 2412 remains level or untilted. Alternatively, the cross-sectional size and/or shape of the connecting arms 2416 can be varied and/or the material varied to cause the same or similar effect.

An accommodating artificial ocular lens (AAOL) device can be configured to both tilt the lens optic portion and laterally shift the center of the lens optic portion in some applications by combining the features described above.

To make the custom accommodating artificial ocular lens (AAOL) device according to the present invention, the patient's eye must be carefully analyzed, measured and mapped to determine the specifications of the accommodating artificial ocular lens (AAOL) device to be manufactured. Specifically, the following is a list of specifications of the accommodating artificial ocular lens (AAOL) device to be considered and then specified, including but not limited to:

| | | |
|---|---|---|
| 1) refraction | Exact Diopter (D) to 0.00 D | |
| 2) diffraction | | |
| 3) aspheric | yes/no, any special degree | |
| 4) presbyopia | yes/no | |

-continued

| | | |
|---|---|---|
| 5) multifocal optic | 50 cm to infinity | |
|   bifocal | | |
|   trifocal | | |
|   accommodating IOL | 38 cm to infinity | |
|   combinations | 19 cm to infinity | |
|   bifocal | | |
|   trifocal | | |
| 6) astigitism | | |
|   how much | diaopters | |
|   where located | degrees | |
|   what shape | many | |
| 7) Aberration | | |
|   cornea | | |
|   lens | | |
|   retina | | |
|   combined | | |
|   what shape | | |
|   where located | | |
|   how much | | |
| 8) optic | | |
|   size | 2.5 to 7 mm | |
|   shape | round elliptical other | |
|   location | centered or decentered | |
|   where | degrees | |
|   concentric | yes/no | |
|   symmetrical | yes/no | |
| 9) overall lens size | made to fit eye or bag | |
|   shape    round | 8 to 15 mm | |
|               elliptical | 8 to 15 mm | |
|               other | 8 to 15 mm | |
| 10) lens optic material | | |
|   silicone | clear | yellow |
|   acrylic | clear | yellow |
|   soft polyimide | clear | yellow |
|   hard polyimide | clear | yellow |
|   PMMA | clear | colorless |
|   Collagen-containing polymer | clear | yellow |
|   blue light blocking additive* | | |
| 11) lens haptic material | | |
|   silicone | | |
|   acrylic | | |
|   soft polyimide | | |
|   collagen-containing polymer | | |
| 12). transmission of date | eye model data, topography- | |
|   manufacturing IOL from data | trace data | |
|   testing IOL from data | | |
| 13) any other special and/or | | |
|   custom features | | |

*yellow is the blue light blocking mechanism

Example 2

The following is an example of a patient information request form to gather information for prescribing and specifying a custom accommodating artificial ocular lens (AAOL) device according to the present invention.

| | | | |
|---|---|---|---|
| 1) Dr. Name | | | |
| 2) Dr. Practice Name | | | |
| 3) address | | | |
| 4) phone number e-mail address | | | |
| 5) patient Name | | | |
| 6) patient Code | | | |
| 7) which Eye | OS | OD | Both |
| 8) AC Depth | | | |
| 9) axial length | | | |
| 10) refraction (Exact, 00D) | | | |
| 11) aspheric correction Yes No/Amount | | | |
| 12) presbyopia Yes/No | | | |
|   preferred reading distance | | | |
|   how close up? (19 cm to 50 cm) | | | |
|   which Lens Design | | | |
|   accommodating (38 CM) | | | |
|   multifocal (50 cm) defractive/refractive | | | |

-continued tri-focal/bi focal
   combination (19 cm to 50 cm)
   trifocal/bifocal
 13) astigmatism, describe:
   (amount)
   (location in degree)
   with rule against rule oblique
   other-describe
 14) aberration: Best Zerneky Model
   cornea/lens/retina/total
   amount
   location
   cornea
   spherical aberration
   high order astigmatism
   trefoil
   other describe
 15) other items needed
   pupil concentric/non-concentric
 16) lens construction
   one (1) piece
   two (2) piece
   etc.
 16) material preference (lens optic portion)
   silicone
   acrylic
   collagen-containing polymer
   polyimide (soft type)
   polyimide (hard type)
   PMMA
   blue light blocking additive (yes/no)
 17) material preference (lens haptic portion)
   silicone
   acrylic
   collagen-containing polymer
   polyimide (soft type)
   blue light blocking additive (yes/no)
 18) optical size 2.5 to 7 mm
   overall diameter 8 to 15 mm
 19) optical symmetrical/non-symmetrical/excentric At the eye surgeon's office, the patient's eye is measured using visual field analyzers, eye charts and a topographer/abberometer. The abberometer measures the aberrations in the patient's eye and provides the eye surgeon with a topography map outlining all the aberrations. The eye surgeon uses the abberometer to check where the aberrations are coming from and analyze the data for different pathologies and make changes to the data where necessary. The abberometer is then used to generate a topography map and digital data that will be transferred to the manufacturer in the form of a customized lens order via satellite, internet, telephonic down load, CD ROM, DVD or mail or fax. Abberometer obtains the necessary information by using the Shack Hartman or means, which analyzes multiple beams of light transferred to the retina and then returned back through the eye. Variations of the light are measured against a light standard that would give perfect vision if all the parameters are met. The variation of the light is then compared against the Zerkeny polynomial to determine whether the variations are in the form of low order aberrations usually spherical and cylinder (toric) or high order aberrations such coma; trefoil (shapes showing in the optic system that look like a starburst usually around the periphery of the eye extending toward the center.

This information will then be received by the manufacturer, analyzed for completeness and any other kind of transmission errors. The data received is in the form of data points to be run through a program that to invert or reverse the information, since to correct an optic system requires making points or corrections that are opposite of the actual data received. This data will be run through the program to convert the data converted into machine language that will form a JFL file that will tell any equipment that can have varying cut (the Presitech Optiform with a variable forming tools or the DAC system with its toric generator) to cut a mold pin or optic in a form based on the information received from the eye surgeon's topography/abberometer, Zydekia Chart etc.

The order depending on the method of manufacturing can create a lens optic as part of the shop order or create a mold pin for the shop order in case of silicone manufacturing. The shop order would then go through the manufacturing process for developing lenses and a final lens optic would be made. During the process the lens would be marked in a manner so that the eye surgeon doing the surgery can tell where on the lens optic the changes are made. One side of the optic can contain all the changes needed for a multi-focal, toric and/or wavefront corrections, or some changes can be on the front side and some on the back side of the accommodating artificial ocular lens (AAOL) device depending on the patient and manufacturing constraints. In order to know that what was manufactured is what was ordered, similar equipment would be used to generate the data such as an abberometer using the same theoretical method to measure the reverse aberrations created in the lens and compare it with the original input information. The accommodating artificial ocular lens (AAOL) device is then sterilized and sent to the eye surgeon.

The manufactured lens data can be sent back with the lens to the eye surgeon, including data points and topography map with a manufacturing certificate for the eye surgeon and patient similar to a patient ID card, instead it would have a topography of the lens on the card.

The eye surgeon then inserts the lens haptic and lens optic into the patient's eye and places the accommodating artificial ocular lens (AAOL) device where needed based on what was ordered received. Minor adjustments in the lens optic and lens haptic can be made to obtain the appropriate axis of the optic. It is possible to make and optic off center in a mold pin combination if it were determined up front exactly where and if the optic needed to be changed from its center point. It is also possible to put adjustments items on the optic and haptic whereby the optic could be shifted up, down or side ways so that the multi-focal, toric, wave front can be lined up to give the patient better vision.

Lens Operation

The accommodating artificial ocular lens (AAOL) device according to the present invention is configured to bow or flex due to forces applied by the eye to the accommodating artificial ocular lens (AAOL) device, in particular to forces applied to the edge portions of the lens plate haptic portion.

The accommodating artificial ocular lens (AAOL) device according to the present invention can be located potentially in the anterior chamber and/or posterior chamber of the eye. Preferably the accommodating artificial ocular lens (AAOL) device according to the present invention in located in the posterior chamber of they eye, and more preferably is located in the capsular bag of the eye after cataract lens removal.

In operation, forces that are exerted on the capsular bag by the zonules of the eye are applied to the accommodating artificial ocular lens (AAOL) device according to the present invention, in particular to the peripheral edges thereof. As forces are applied to the outer edges of the accommodating artificial ocular lens (AAOL) device according to the present invention by the eye, the lens plate haptic portion begins to bow in an arch generally perpendicular to the flexible or resilient lens arm portions connecting the lens optic portion to the lens plate haptic portion so as to move the lens optic portion either forward or rearward from a resting position depending on the particular configuration and arrangement. In any event, the accommodating artificial ocular lens (AAOL) device according to the present invention is configured so that the lens plate haptic portion moves the lens optic portion during operation.

The operation or functioning of the accommodating artificial ocular lens (AAOL) device 10 according to the present invention is shown in FIGS. 23-26.

Figure 23:
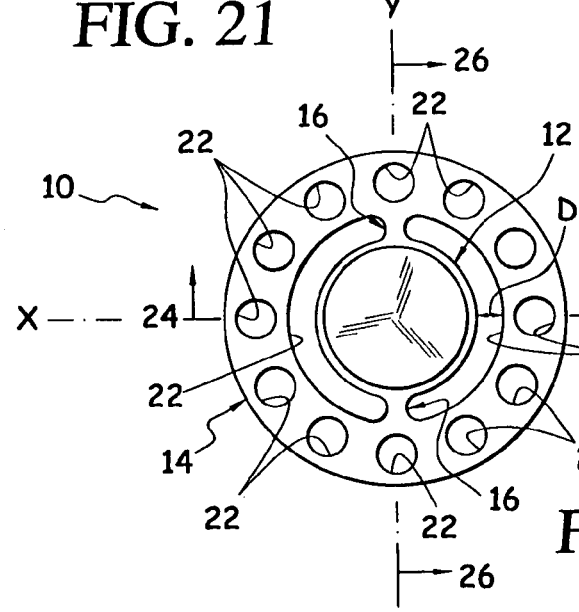
FIG. 23 is a top planar view of the accommodating artificial ocular lens (AAOL) device shown in FIG. 2 in a resting or unstressed condition.
Figure 24:
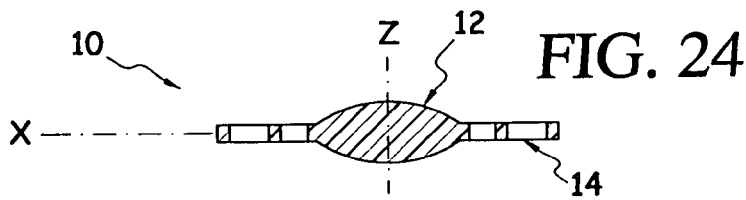
FIG. 24 is a center cross-sectional view of the accommodating artificial ocular lens (AAOL) device, as indicated in FIG. 23.
Figure 25:
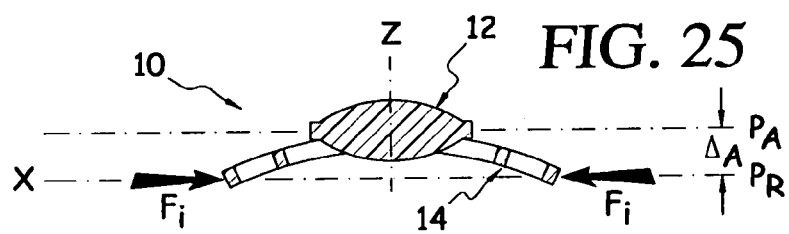
FIG. 25 is a center cross-sectional view of the accommodating artificial ocular lens (AAOL) device shown in FIG. 24 in a stressed condition showing the lens plate haptic portion bowing and the lens optic portion moving along the optical axis Z of the eye.
Figure 26:
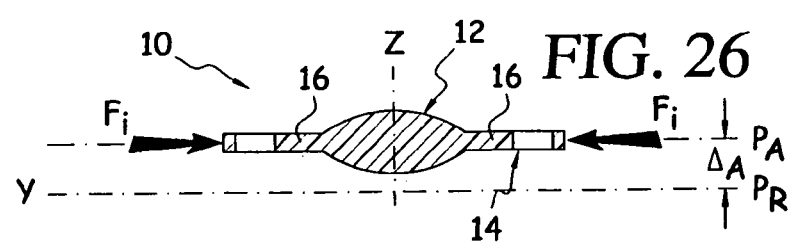
FIG. 26 is a center cross-sectional view of the accommodating artificial ocular lens (AAOL) device as indicated in FIG. 23, along the transverse axis Y.

The accommodating artificial ocular lens (AAOL) device 10 is shown in an unstressed and unbowed condition, as shown in FIGS. 23 and 24. When inwardly directed forces $F_i$ are applied around the perimeter of the plate haptic portion 14, the plate haptic portion 14 begins to bow relative to the X axis as illustrated in FIG. 25, and may furthermore be enhanced by varying hydraulic pressures in the eye. In this manner, the lens portion 12 is moved from a resting position plane $P_R$ to an accommodating plane $P_A$ and traverses a distance $\Delta_A$. However, as illustrated in FIG. 26, the plate haptic portion 14 does not bow or substantially bow along the tranverse axis Y, since the flexible or resilient lens arm portions 16, 16 reinforce and stiffen the lens plate haptic portion 14 from bowing along this tranverse axis Y. Thus, the accommodating artificial ocular lens (AAOL) device 10 essentially bows in only a single dimension, and not in two (2) dimensions.

As illustrated in FIG. 25, the outer edges of the lens optic portion 12 become somewhat separated and exposed from the upper surface of the lens plate haptic portion 14 due to bowing of the lens plate haptic portion 14. In this manner, it is possible that the lens optic portion 12 could potentially extend into or through the pupil of the iris of the eye. However, as illustrated in FIG. 26, the lens arm portions 16, 16 do not allow the lens plate haptic portion 14 to bow in the tranverse axis Y, and prevents the lens optic portion 12 from being exposed and separating from the upper surface of the plate haptic portion 14. Further, the arm portion 16 acts or functions like a pair of bumpers against the back of the iris at the opening of the pupil to prevent the lens optic portion 12 from entering into or passing through the pupil of the iris of the eye.

As illustrated in FIGS. 55 and 56, the lens optic portion 2512 remains flat in the X-Y plane even when the lens haptic portion 2514 is significantly bowed or bent due to the highly flexible nature of the connecting arms 2516. Further, the lens haptic portion 2514 can be provided with one or more marks 2515 (e.g. ink or indent) to facilitate placement and alignment when implant into the eye.

While this invention has been described with respect to various specific examples and embodiments, it is to be understood that the invention is not limited thereto and that it can be variously practiced within the scope of the following claims.

We claim:

1. An accommodating intraocular lens device configured to be implanted into a capsular bag of an eye after cataract lens removal, said lens device comprising:
   a circular-shaped lens optic configured to be initially located in a reference plane oriented substantially perpendicular to a central focal axis of the eye when said lens device is implanted into the eye;
   a substantially planar bowing lens plate haptic surrounding said lens optic with at least one circular-shaped through opening separating and spacing apart said lens optic a predetermined distance from said lens plate haptic; said lens plate haptic configured to bow in only a length dimension of said lens plate haptic when force is applied by the eye inwardly on opposite edges of said lens plate haptic, said lens plate haptic being located in said reference plane, said lens optic and said lens plate haptic being configured to fit within the capsular bag of the eye after cataract removal; and
   a lens connection configured to connect said lens optic to said lens plate haptic, said lens connection configured to move said lens optic in and out of said reference plane in a manner to focus the eye when force is applied by the eye inwardly to said opposite edges of said lens plate haptic causing said lens plate haptic to bow, said lens connection being defined by a pair of flexible arms connecting said lens optic to said lens plate haptic at opposite ends of said lens optic along a first axis located in said reference plane oriented substantially perpendicular to a second axis located in said reference plane along which said force is applied by the eye inwardly to said opposite edges of said lens plate haptic, said lens connection configured to move said lens optic in and out of said reference plane in a manner to focus the eye when force is applied by the eye inwardly to said opposite edges of said lens plate haptic and/or eye pressure is increased behind said intraocular lens device causing said lens plate haptic to bow.

2. A lens device according to claim 1, wherein said lens optic is separated and spaced apart a distance from said lens haptic by at least one circular-shaped opening.

3. A lens device according to claim 1, wherein said lens connection is configured to prevent bowing of said lens optic when said lens haptic is being bowed.

4. A lens device according to claim 1, wherein said pair of flexible arms is initially located in said reference plane.

5. A lens device according to claim 1, wherein each said arms extends from an outer edge of said lens optic to an inner edge of said lens plate haptic.

6. A lens device according to claim 1, wherein said lens optic is a substantially rectangular-shaped lens optic separated and spaced apart a predetermined distance from said lens haptic by a set of partial oval-shaped openings.

7. A lens device according to claim 1, wherein said lens plate haptic is provided with at least one peripheral through hole configured to facilitate anchoring of an edge of said lens plate haptic within the eye.

8. A lens device according to claim 1, wherein at least a portion of an edge of said lens plate haptic is provided with an edge finish configured to facilitate anchoring of said edge of said lens plate haptic within the eye.

9. A lens device according to claim 8, wherein said edge finish is at least one selected from the group consisting of scallops, serrations, notches, pins, and flaps.

10. A lens device according to claim 1, wherein said lens optic is centered between said opposite edges of said lens plate haptic portion.

11. A lens device according to claim 1, wherein said lens optic is not centered between said opposite edges of said lens plate haptic.

12. A lens device according to claim 1, wherein a center of said lens optic is located along said second axis.

13. A lens device according to claim 12, wherein said lens optic is centered between said opposite edges of said lens plate haptic.

14. A lens device according to claim 12, wherein said lens optic is not centered between said opposite edges of said lens plate haptic.

15. A lens device according to claim 1, wherein a center of said lens optic is located off axis relative to said second axis.

16. A lens device according to claim 1, wherein said lens device is made from at least one material selected from the group consisting of silicone, collagen based polymer, polymethyl methacrylate, acrylic polymer, polyimide, polyamide, polyester, and polysulfone.

17. A lens device according to claim 1, wherein said lens device is configured to bow only relative to said first axis.

18. A lens device according to claim 17, wherein said lens device is configured not to bow relative to said second axis oriented transverse relative to said first axis.

19. A lens device according to claim 1, wherein said lens optic is also a toric lens optic.

20. A lens device according to claim 1, wherein said lens optic is also a wavefront lens optic.

21. A lens device according to claim 19, wherein said lens optic is also a wavefront lens optic.

22. A lens device according to claim 1, wherein said lens optic is a multi-focal lens optic.

* * * * *